(12) United States Patent
Akagi

(10) Patent No.: US 7,031,429 B2
(45) Date of Patent: Apr. 18, 2006

(54) MAMMOGRAPHY SYSTEM AND METHOD FOR MANAGING INFORMATION

(75) Inventor: Eiichi Akagi, Hachioji (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 156 days.

(21) Appl. No.: 10/825,553

(22) Filed: Apr. 14, 2004

(65) Prior Publication Data

US 2004/0213372 A1 Oct. 28, 2004

(30) Foreign Application Priority Data

Apr. 24, 2003 (JP) ............................. 2003-120246

(51) Int. Cl.
*A61B 6/04* (2006.01)
(52) U.S. Cl. ........................................ 378/37; 378/165
(58) Field of Classification Search .................. 378/37, 378/62, 165, 193, 197, 198, 207
See application file for complete search history.

(56) References Cited

U.S. PATENT DOCUMENTS

2004/0086164 A1* 5/2004 Moriyama et al. .......... 382/131
2004/0240624 A1* 12/2004 Shiibashi et al. ........... 378/197
2005/0213702 A1* 9/2005 Akagi ......................... 378/37

FOREIGN PATENT DOCUMENTS

JP 2003-088515 3/2003

\* cited by examiner

*Primary Examiner*—David V. Bruce
*Assistant Examiner*—Courtney Thomas
(74) *Attorney, Agent, or Firm*—Frishauf, Holtz, Goodman & Chick, P.C.

(57) ABSTRACT

A mammography system has: a mammography apparatus for radiographing a mamma image of a patient by irradiating radiations and for recording the mamma image in a cassette; a reading apparatus for reading the mamma image from the cassette; and a controller for obtaining the read mamma image by controlling the reading apparatus, wherein the mammography apparatus comprises a communication section for transmitting radiography performance information to the controller, the radiography performance information including first key information, and the controller comprises: a storage section for storing the radiographing order information including second key information; and a controlling section for relating the radiography performance information and the radiographing order information based on the first key information included in the radiography performance information transmitted from the mammography apparatus and the second key information included in the stored radiographing order information.

30 Claims, 16 Drawing Sheets

HOME POSITION
(ROTATION ANGLE 0°)

DETECTED ANGLE (-)30°

HOME POSITION
(ROTATION ANGLE 0°)

DETECTED ANGLE (+)30°

FIG.6

| ORDER ID | RADIOGRAPHING ORDER INFORMATION ||||| RADIOGRAPHY INFORMATION ||| RADIOGRAPHY PERFORMANCE INFORMATION ||||
| | PATIENT INFORMATION |||| RADIOGRAPHIC PART /DIRECTION | RADIOGRAPHY DATE | ... | CASSETTE ID | RADIOGRAPHIC PART /DIRECTION | TUBE VOLTAGE (kV) | COMPRESSION AMOUNT (mm) | ... |
| | PATIENT ID | NAME | AGE | ... | | | | | | | | |
| 0001 | 1001 | HANAKO YAMADA | 40 | ... | LCC | 2003/4/1 | ... | 1010101 | | | | ... |
| 0002 | 1001 | HANAKO YAMADA | 40 | ... | LM | 2003/4/1 | ... | 1010102 | LM | 60 | 10 | ... |
| 0003 | 1001 | HANAKO YAMADA | 40 | ... | RCC | 2003/4/1 | ... | 1010103 | | | | ... |
| 0004 | 1001 | HANAKO YAMADA | 40 | ... | RM | 2003/4/1 | ... | 1010104 | | | | ... |
| 0005 | 2050 | KYOKO SUZUKI | 50 | ... | LCC | 2003/4/1 | ... | - | | | | ... |
| ... | ... | ... | ... | ... | ... | ... | ... | ... | ... | ... | ... | ... |

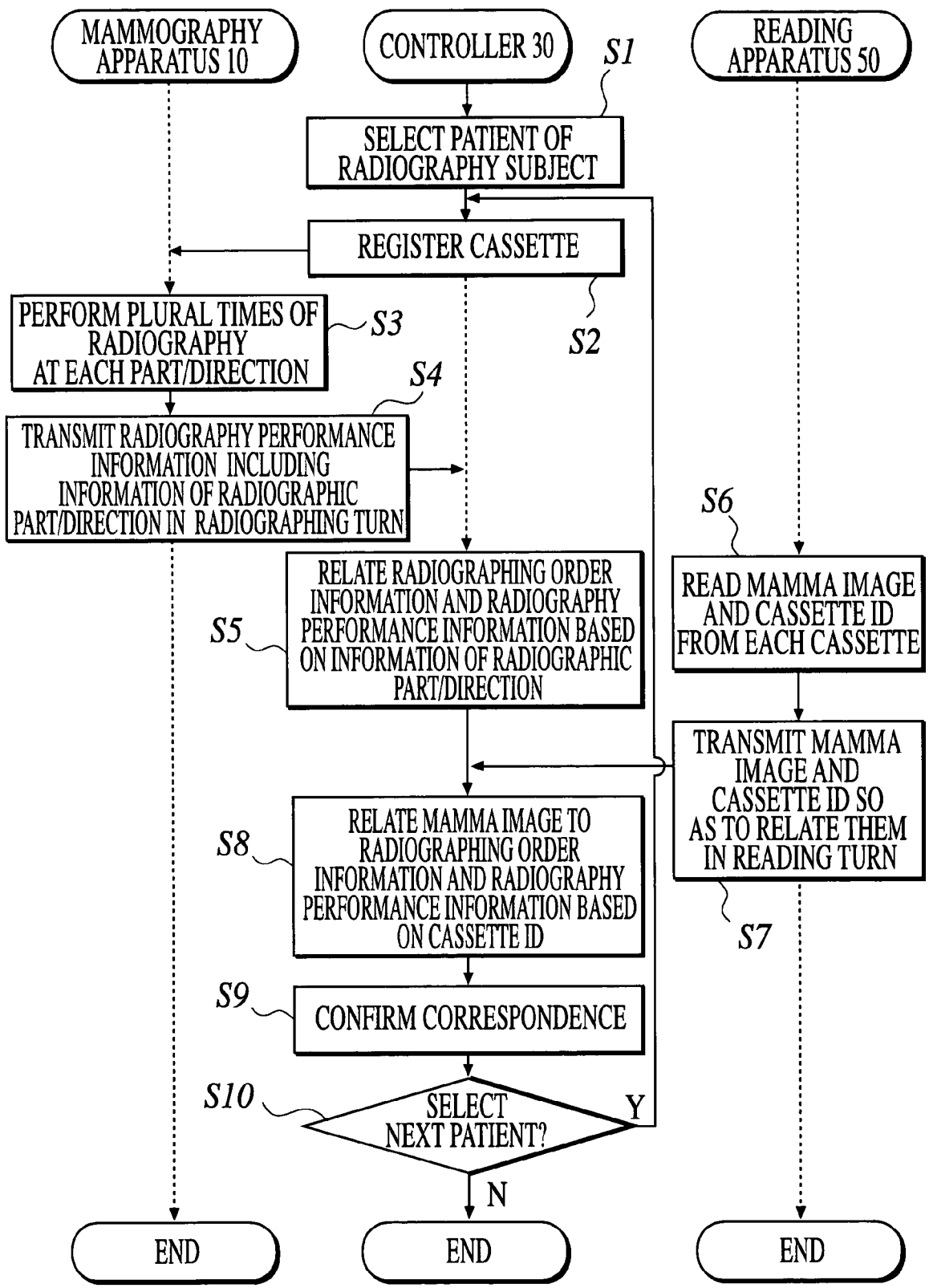

FIG.8

| RADIOGRAPHING TURN | RADIOGRAPHY PERFORMANCE INFORMATION | RADIOGRAPHING ORDER INFORMATION | CASSETTE ID | MAMMA IMAGE | CASSETTE ID |
|---|---|---|---|---|---|
| 1 | W — RM | A — RCC | 10101 | mam1.jpg | 10102 |
| 2 | X — RCC | B — RM | 10102 | mam2.jpg | 10103 |
| 3 | Y — LCC | C — LCC | 10103 | mam3.jpg | 10101 |
| 4 | Z — LM | D — LM | 10104 | mam4.jpg | 10104 |

CASE OF RADIOGRAPHING IN UP-DOWN DIRECTION(CC)

FIG.12A  CASE OF RADIOGRAPHING IN-OUT DIRECTION(M) WHEN ATTACHED TO CASSETTE
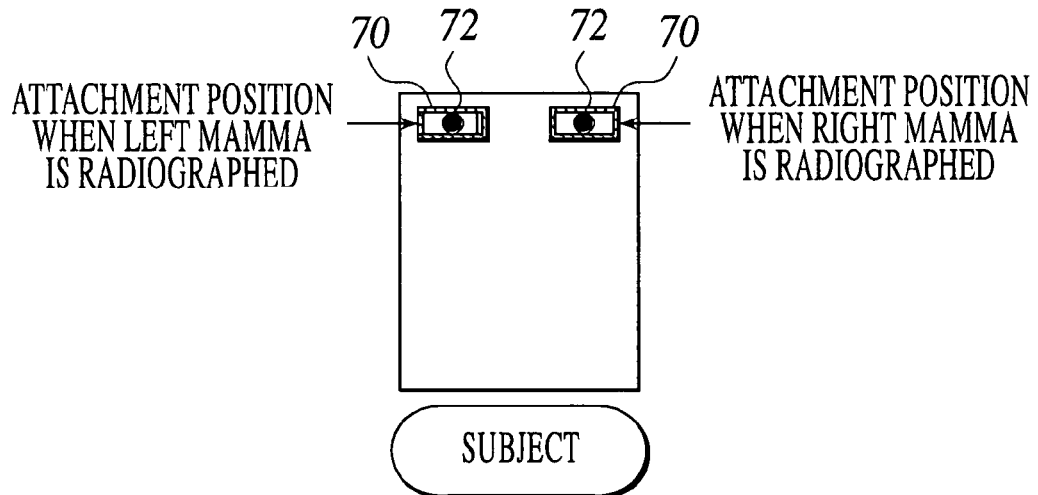
FIG.12B
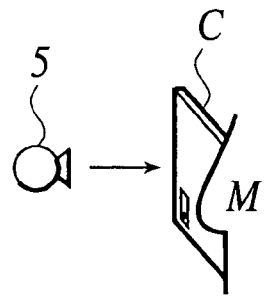
RADIOGRAPHING LEFT MAMMA
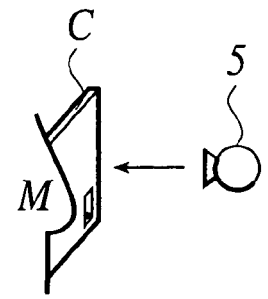
RADIOGRAPHING RIGHT MAMMA
FIG.12C
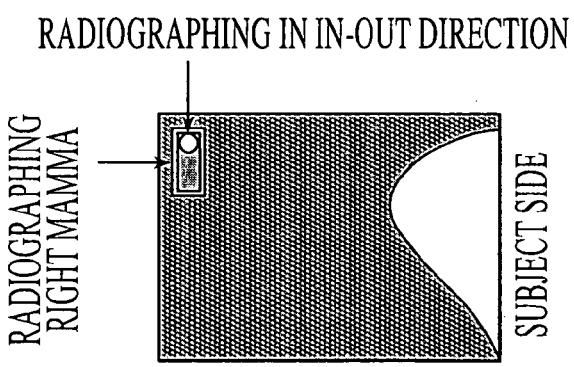

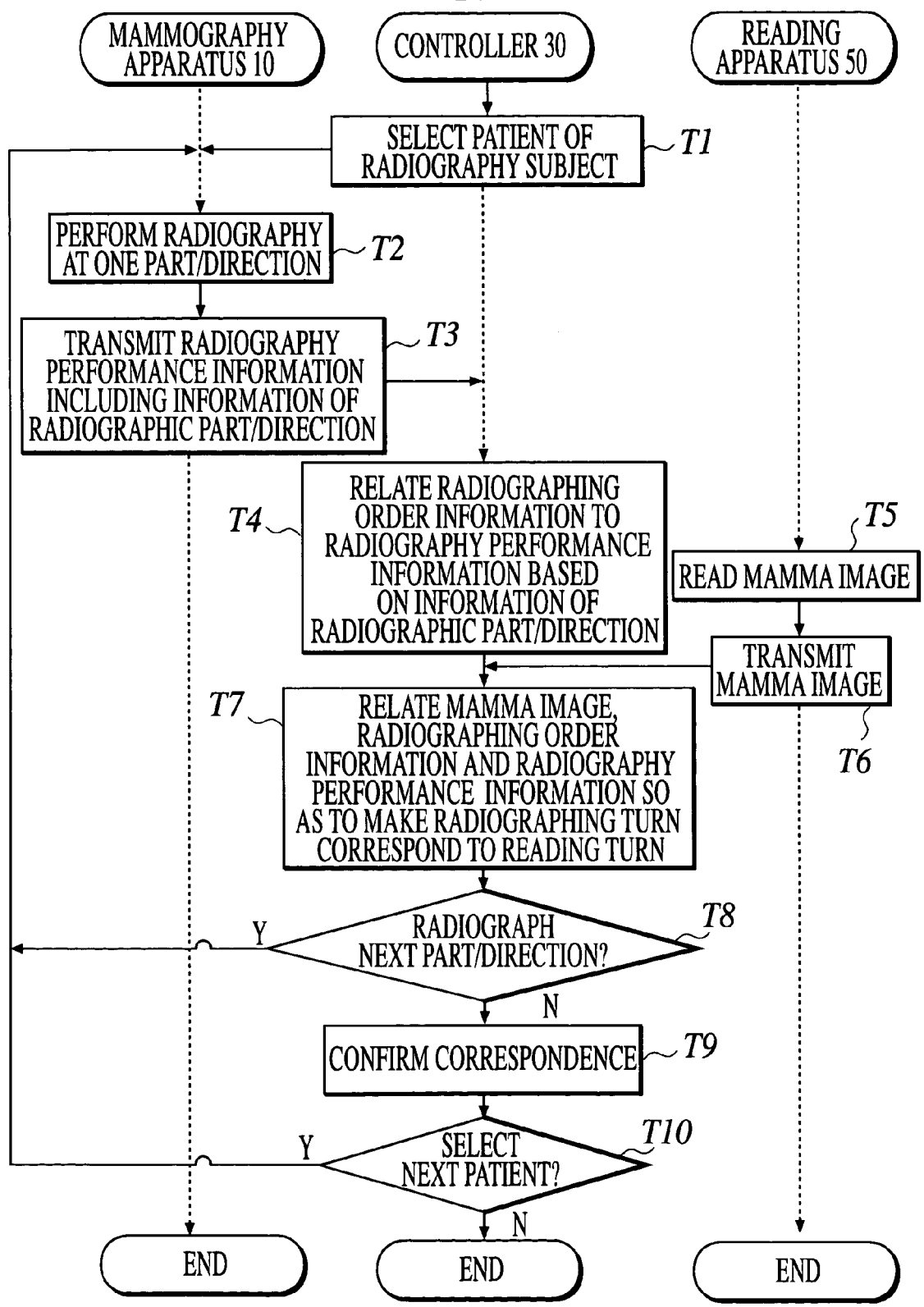

FIG.15A
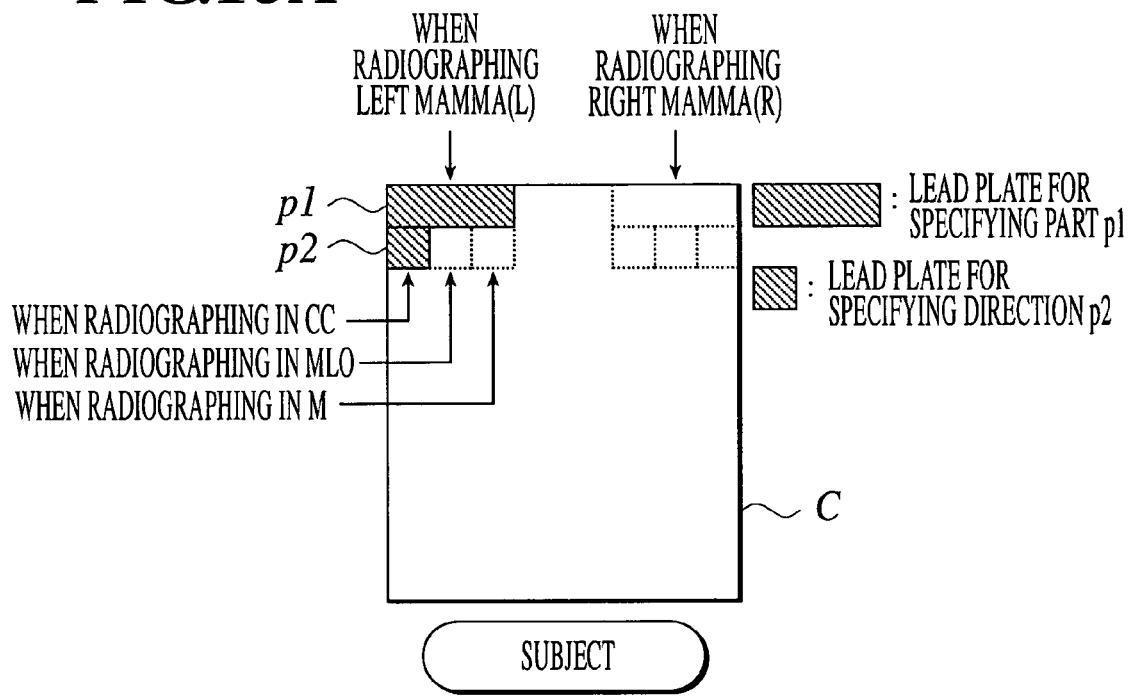
FIG.15B   FIG.15C   FIG.15D
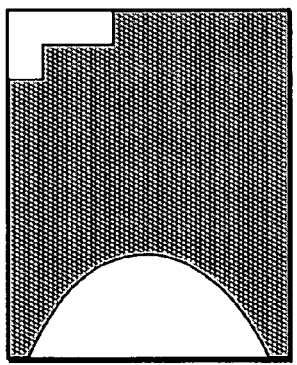 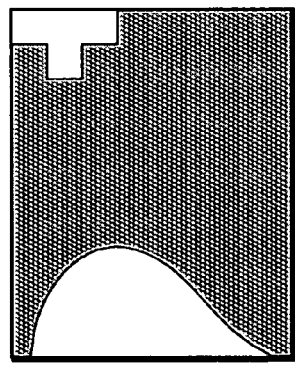 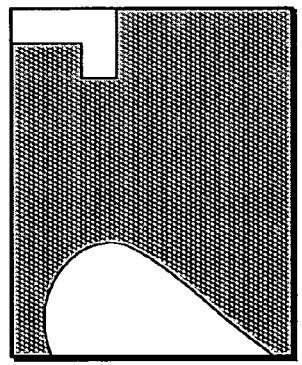
LCC RADIOGRAPHING   LMLO RADIOGRAPHING   LM RADIOGRAPHING

MAMMOGRAPHY SYSTEM AND METHOD FOR MANAGING INFORMATION

BACKGROUND OF THE INVENTION

1. Field of the Invention

The invention relates to a mammography system for radiographing a mamma image and an information managing method for managing a radiographed mamma image, radiographing order information and radiography performance information.

2. Description of Related Art

An image obtained with radiography has been widely used as a medical image for diagnosis, and recently, digitization of medical images have been achieved. For example, a CR (Computed Radiography) device is used to obtain an image signal by making a phosphor plate in which a photostimulable phosphor layer is formed to absorb radiations having transmitted through a subject, scanning the phosphor plate with laser beam to emit radiation energy accumulated in the phosphor layer, and photoelectrically converts the emitted light.

Conventionally, when a radiation image of a patient is radiographed, radiography for each patient is managed by a radiographic technician recording radiography performance information such as radiation exposure-amount, a radiographic part/direction and the like at the time of radiography on a management paper, and later a manager collecting the management paper and inputting the radiography performance information to a Hospital Information System (hereafter, it is referred to as HIS) for managing information in a hospital or a Radiology Information System (hereafter, it is referred to as RIS) for managing information in a department of radiology to make a database. However, in this management method, since it is necessary to record radiography performance information at each time of radiography and further to input the recorded radiography performance information to HIS, the operation procedure is complicated.

In recent years, utilized is a radiography system capable of simplifying a radiography management operation by connecting a radiographing apparatus and a controller through a communication network, the controller for controlling a radiography operation of the radiographing apparatus, obtaining radiography performance information at the controller from the radiographing apparatus online, and uploading the obtained radiography performance information to HIS (for example, see Japanese Patent Application Publication (Unexamined) No. Tokukai 2003-88515).

With reference to FIG. 16, the above-mentioned radiography system will be described.

The radiography system using the photostimulable phosphor is largely classified into an exclusive type which incorporates a phosphor plate therein for performing both radiography and reading an image, and a cassette type which is carriageable and holds a phosphor plate. A radiography method with the cassette type will be described with reference to FIG. 16.

As shown in FIG. 16, a mammography system of the cassette type comprises a radiographing apparatus for radiographing a medical image of a patient with the use of a cassette, a reading apparatus for reading the medical image from the cassette, and a controller for obtaining the read medical image by controlling the reading apparatus. The controller is structured to be capable of communicating with HIS or RIS.

In the radiography system having the above-mentioned structure, before radiography, according to a request from a doctor, radiographing order information is issued, the radiographing order information including patient information such as a patient name of a radiography subject, sex and the like, radiography instruction information such as a radiographic part, a radiographic method and the like, examination information and the like. The issued radiographing order information is delivered to the controller. At the controller, the radiographing order information is displayed in a list form at the time of radiography.

Hereinafter, a workflow of radiography in the radiography system will be described.

1. A radiographic technician selects radiographing order information which radiography is to be performed based on, among radiographing order information displayed in a list form at the controller. Here, the selection may be made either before the radiography or after the radiography.

2. In order to clarify correspondence of a cassette to be used for the radiography and radiographing order information, the radiographic technician performs an operation called cassette registration. In the cassette, identification information (hereafter, it is referred to as cassette ID) for identifying the cassette from the other cassettes is placed. In the cassette registration operation, the radiographic technician inputs a cassette ID of the cassette to be related to the selected radiographing order information, to the controller. At the controller, as well as the selected radiographing order information is displayed, the selected radiographing order information and the inputted cassette ID are related to each other. Here, the cassette registration may be performed after the radiography. The former way of performing cassette registration before radiography is called pre-registration, and the latter way of performing cassette registration after radiography is called post-registration.

3. The radiographic technician looks at the displayed radiographing order information to confirm a patient of a radiography subject, a radiographic part and the like, and perform radiography at a radiographing apparatus. With radiations irradiated in the radiographing apparatus, a radiation image is recorded in the cassette and radiographing performance information is transmitted to the controller.

4. The radiographic technician sets the cassette to the reading apparatus and has the reading started. In the reading apparatus, a medical image and a cassette ID are read from the cassette, and the read medical image and the read cassette ID are related to each other and transmitted to the controller.

5. In the controller, the selected radiographing order information is related to the radiographing performance information transmitted from the radiographing apparatus. In addition, the medical image transmitted from the reading apparatus is related to the radiographing order information. After all, the medical image is related to the radiographing order information and the radiography performance information, and these related information is transmitted to HIS or RIS as accompanying information of the medical image.

However, in the above-described method, since a radiographic technician always has to select radiographing order information to which radiographing performance information is to be related, the selecting operation is complicated. In particular, if a mamma image is to be radiographed, generally, radiography is performed to one patient at different radiographic parts and in different radiographic directions, such as a left mamma in up-down direction, in in-out direction, a right mamma in up-down direction, in in-out direction. In this case, it is necessary that, at each time of radiography, after the radiographic technician travels to the reading apparatus and sets the cassette to the reading apparatus, he/she again has to return to the controller for selecting radiographing order information and travel to the radiographing apparatus. Therefore, efficiency of radiography operation is poor.

SUMMARY OF THE INVENTION

An object of the present invention is to make radiography operation of a mamma image more efficient by automatically relating each information of a mamma image, radiographing order information and radiography performance information.

In accordance with a first aspect of the present invention, a mammography system comprises: a mammography apparatus for radiographing a mamma image of a patient by irradiating radiations and for recording the mamma image in a cassette; a reading apparatus for reading the mamma image from the cassette; and a controller for obtaining the read mamma image by controlling the reading apparatus, the controller being connected to the mammography apparatus and the reading apparatus, wherein the mammography apparatus comprises a communication section for transmitting radiography performance information to the controller, the radiography performance information including first key information for relating the radiography performance information and radiographing order information to each other, and the controller comprises: a storage section for storing the radiographing order information including second key information for relating the radiography performance information and the radiographing order information to each other; and a controlling section for relating the radiography performance information and the radiographing order information based on the first key information included in the radiography performance information transmitted from the mammography apparatus and the second key information included in the stored radiographing order information.

According to the system of the first aspect, since radiographing order information and radiography performance information are related to each other based on key information, it is possible to omit an operation to select radiographing order information to be related to radiography performance information in the controller. Therefore, it is not necessary for a radiographic technician to travel to the controller for the selecting operation at the controller, and thereby, at mamma image radiography in particular, which often requires performing a plurality of times of radiography corresponding to different radiographic parts and different radiographic directions, it is possible to improve efficiency of a radiography operation.

Preferably, in the system of the first aspect of the present invention, the reading apparatus comprises a communication section for reading the mamma image and identification information of the cassette from the cassette, for relating the identification information of the cassette to the mamma image, and for transmitting the related mamma image and the related identification information of the cassette, to the controller; the controller comprises an identification information input section for inputting the identification information of the cassette to be used in radiography; and the controlling section relates the inputted identification information of the cassette to the radiographing order information, and relates the mamma image, the radiographing order information and the radiography performance information to one another based on the identification information of the cassette related to the radiographing order information and the identification information of the cassette related to the mamma image transmitted from the reading apparatus.

According to the above-mentioned system, since, based on identification information of a cassette, radiographing order information and a mamma image are related to each other, and the mamma image, the radiographing order information and radiography performance information are related to one another, it is possible to relate the radiographing order information and the radiography performance information as accompanying information according to the mamma image. Thereby, it is possible to manage images accurately.

Preferably, in the system of the first aspect of the present invention, the communication section in the mammography apparatus transmits the radiography performance information including the first key information to the controller at each time of radiography, the reading apparatus comprises a communication section for transmitting the mamma image to the controller at each time of reading the mamma image, and the controlling section in the controller relates the radiographing order information and the radiography performance information to each other based on the first key information and the second key information, and relates the mamma image, the radiographing order information and the radiography performance information to one another so as to make a radiographing turn of the mamma image correspond to a reading turn of the mamma image.

According to the above-mentioned system, since radiographing order information and radiography performance information are related to each other based on key information, and a mamma image, the radiographing order information and the radiography performance information are related to one another so as to make a radiographing turn correspond to a reading turn, it is possible to relate each information without using identification information of a cassette.

Preferably, in the system of the first aspect of the present invention, the first key information and the second key information include information of at least one of a radiographic part and a radiographic direction.

According to the above-mentioned system, at mamma image radiography, which often requires performing a plurality of times of radiography corresponding to different radiographic parts and different radiographic directions, a radiographic part and/or a radiographic direction, which are/is information especially effective to relate radiographing order information and radiography performance information to each other, can be used as key information.

Preferably, in the system of the first aspect of the present invention, the mammography apparatus comprises: an angle detecting section for detecting an angle of a radiographic platform to place a subject on; and a determination section for determining at least one of the radiographic part and the radiographic direction based on the detected angle, and the communication section in the mammography apparatus transmits the information of at least one of the radiographic part and the radiographic direction as the first key information to the controller.

According to the above-mentioned system, it is possible to determine a radiographic part and/or a radiographic direction, which is/are used as key information, by detecting an angle of a radiographic platform.

Preferably, in the system of the first aspect of the present invention, the mammography apparatus comprises an angle detecting section for detecting an angle of a radiographic platform to place a subject on, and the controller comprises a determination section for determining at least one of the radiographic part and the radiographic direction based on information of the detected angle.

According to the above-mentioned system, it is possible to determine a radiographic part and/or a radiographic direction in the controller according to the detected angle of the radiographic platform in the mammography apparatus.

Preferably, in the system of the first aspect of the present invention, the mammography apparatus comprises a part/direction input section for inputting the information of at least one of the radiographic part and the radiographic direction, and the communication section in the mammography apparatus transmits the inputted information of at least one of the radiographic part and the radiographic direction as the first key information to the controller.

According to the above-mentioned system, the inputted information of a radiographic part and/or a radiographic direction can be used as key information.

Preferably, in the system of the first aspect of the present invention, the first key information and the second key information include left-right information for indicating whether the radiographic part is a right mamma or a left mamma, the communication section in the mammography apparatus transmits the radiography performance information including the left-right information to the controller, the storage section in the controller stores the radiographing order information including the left-right information for indicating whether the radiographic part is the right mamma or the left mamma, and the controlling section in the controller relates the radiography performance information and the radiographing order information based on the left-right information included in the radiography performance information transmitted from the mammography apparatus and the left-right information included in the stored radiographing order information.

According to the above-mentioned system, when one time of radiography is performed on a right mamma and a left mamma, respectively, corresponding to one patient, or when a plurality of times of radiography corresponding to a plurality of radiographic directions are performed on a right mamma and a left mamma, respectively, radiography is performed on a right mamma and a left mamma alternately in general. Therefore, it is possible to relate radiographing order information and radiography performance information according to only left-right information.

Preferably, in the system of the first aspect of the present invention, the mammography apparatus comprises a left-right information input section for inputting the left-right information.

According to the above-mentioned system, it is possible for a radiographic technician to input left-right information at the mammography apparatus.

Preferably, in the system of the first aspect of the present invention, the communication section in the mammography apparatus transmits information indicating a radiographing turn of the mamma image as the first key information to the controller, the controller comprises a radiographing turn input section for inputting the radiographing turn of radiography to be performed based on the radiographing order information, the storage section in the controller stores the radiographing order information and the inputted radiographing turn so as to relate the radiographing order information and the inputted radiographing turn to each other, and the controlling section in the controller relates the radiographing order information and the radiography performance information to each other so as to make the radiographing turn included in the radiography performance information transmitted from the mammography apparatus correspond to the radiographing turn related to the stored radiographing order information.

More preferably, the communication section in the reading apparatus transmits the mamma image read from the cassette in a reading turn of the mamma image from the cassette, and the controlling section in the controller relates the mamma image, the radiographing order information and the radiography performance information to one another so as to make the radiographing turn of the mamma image correspond to the reading turn of the mamma image.

According to the above-mentioned system, since radiographing order information and radiography performance information are related to each other based on information of a radiographing turn as key information and an inputted radiographing turn of radiography to be performed based on radiographing order information, and a mamma image, the radiographing order information and the radiography performance information are related to one another so as to make the radiographing turn correspond to the reading turn, even in the case of continuously performing a plurality of times of radiography with the radiographing turn inputted in advance, it is automatically relate the mamma image, the radiographing order information and the radiography performance information to one another. Therefore, it is not necessary for a radiographic technician to travel to the reading apparatus to insert a cassette, and thereby it is possible to improve efficiency of a radiography operation.

Preferably, in the system of the first aspect of the present invention, the controller comprises a display section for displaying correspondence among the mamma image, the radiographing order information and the radiography performance information that are related to one another by the controlling section.

According to the above-mentioned system, it is possible to easily confirm correspondence among the mamma image, the radiographing order information and the radiography performance information that are related to one another.

Preferably, in the system of the first aspect of the present invention, radiography is performed with a part/direction specifier attached to the cassette, the part/direction specifier indicating a radiographic part and a radiographic direction in the mamma image.

According to the above-mentioned system, with the part/direction specifier, it is possible for a radiographic technician to easily determine a radiographic part and a radiographic direction in a radiographed mamma image. Therefore, it is possible to manage mamma images more accurately. Further, since the part/direction specifier is attached to a cassette to be used, it is not necessary to change a structure of the cassette. Therefore, it is possible to easily determine a radiographic part and radiographic direction with cost reduced.

Preferably, in the system of the first aspect of the present invention, radiography is performed with a part/direction specifier attached to one of the radiographic platform of the mammography apparatus and a pressure plate for compressing a mamma, the part/direction specifier indicating a radiographic part and a radiographic direction in the mamma image.

According to the above-mentioned system, with the part/direction specifier, it is possible for a radiographic technician to easily determine a radiographic part and a radiographic technician in a radiographed mamma image. Therefore, it is possible to manage mamma images more accurately. Further, since the part/direction specifier is attached to either a radiographic platform or a pressure plate to be used, it is not necessary to change a structure of the mammography apparatus. Thereby, it is possible to easily determine a radiographic part and a radiographic direction with cost reduced.

In accordance with a second aspect of the present invention, a mammography system comprises: a mammography apparatus for radiographing a mamma image of a patient by irradiating radiations and for reading the mamma image as digital data; and a controller for obtaining the mamma image, the controller connected to the mammography apparatus, wherein the mammography apparatus comprises a communication section for relating radiography performance information to the read mamma image, the radiography performance information including first key information for relating the radiography performance information and radiographing order information, and for transmitting the related radiography performance information and the related mamma image, to the controller, and the controller comprises: a storage section for storing the radiographing order information including second key information for relating the radiography performance information and the radiographing order information; and a controlling section for relating the mamma image, the radiographing order information and the radiography performance information to one another based on the first key information included in the radiography performance information transmitted from the mammography apparatus and the second key information included in the stored radiographing order information.

According to the system of the second aspect, since, based on key information, a mamma image and radiography performance information both transmitted from the mammography apparatus for radiographing and reading a mamma image, and radiographing order information are automatically related to one another, it is possible to omit an operation to select radiographing order information to be related to radiography performance information in the controller. Therefore, it is not necessary for a radiographic technician to travel to the controller for the selecting operation, and thereby, at mamma image radiography in particular, which often requires performing a plurality of times of radiography corresponding to different radiographic parts and different radiographic directions, it is possible to improve efficiency of a radiography operation.

Preferably, in the system of the second aspect of the present invention, the first key information and the second key information include left-right information for indicating whether a radiographic part is a right mamma or a left mamma, the communication section in the mammography apparatus transmits the radiography performance information including the left-right information to the controller, the storage section in the controller stores the radiographing order information including the left-right information, and the controlling section in the controller relates the mamma image, the radiographing order information and the radiography performance information to one another based on the left-right information included in the radiography performance information transmitted from the mammography apparatus and the second key information included in the stored radiographing order information.

According to the above-mentioned system, when one time of radiography is performed on a right mamma and a left mamma, respectively, corresponding to one patient, or when a plurality of times of radiography corresponding to a plurality of radiographic directions are performed on a right mamma and a left mamma, respectively, radiography is performed on a right mamma and a left mamma alternately in general. Therefore, it is possible to relate radiographing order information and radiography performance information according to only left-right information.

In accordance with a third aspect of the present invention, a method for managing information in a mammography system comprising a mammography apparatus for radiographing a mamma image by irradiating radiations and for recording the mamma image in a cassette, a reading apparatus for reading the mamma image from the cassette, and a controller for obtaining the read mamma image by controlling the reading apparatus, the controller being connected to the mammography apparatus and the reading apparatus, the method comprises: transmitting radiography performance information including first key information from the mammography apparatus to the controller, the first key information for relating the radiography performance information and radiographing order information to each other; storing the radiographing order information including second key information in a storage section of the controller, the second key information for relating the radiography performance information and the radiographing order information; and relating the radiography performance information and the radiographing order information to each other based on the first key information included in the radiography performance information transmitted from the mammography apparatus and the second key information included in the stored radiographing order information, in the controller.

According to the method of the third aspect, since radiography performance information and radiography performance information are automatically related to each other based on key information, it is possible to omit an operation to select radiographing order information to be related to radiography performance information in the controller. Therefore, it is not necessary for a radiographic technician to travel to the controller, and thereby, at mamma image radiography in particular, which often requires performing a plurality of times of radiography corresponding to different radiographic parts and different radiographic directions, it is possible to improve efficiency of a radiography operation.

Preferably, the method of the third aspect of the present invention, further comprises: reading the mamma image and identification information of the cassette from the cassette, in the reading apparatus; transmitting the mamma image and the identification information of the cassette to the controller so as to relate the mamma image and the identification information of the cassette to each other; inputting the identification information of the cassette to be used in radiography, in the controller; relating the inputted identification information of the cassette to the radiographing order information, in the controller; and relating the mamma image, the radiographing order information and the radiography performance information to one another based on the identification information of the cassette related to the radiographing order information and the identification information of the cassette related to the mamma image transmitted from the reading apparatus, in the controller.

According to the above-mentioned method, since, based on identification information of a cassette, radiographing order information and a mamma image are related to each other, and the mamma image, the radiographing order information and radiography performance information are related to one another, it is possible to relate the radiographing order information and the radiography performance information as accompanying information according to the mamma image, and thereby, it is possible to manage images accurately.

Preferably, the method of the third aspect of the present invention, further comprises: transmitting the radiography performance information including the first key information to the controller at each time of radiography; transmitting the mamma image to the controller at each time that the reading apparatus reads the mamma image; and relating the mamma image, the radiographing order information and the radiography performance information to one another so as to make a radiographing turn of the mamma image correspond to a reading turn of the mamma image after the radiographing order information and the radiography performance information are related to each other based on the first key information and the second key information.

According to the above-mentioned method, since, based on key information, radiographing order information and radiography performance information are related to each other, and a mamma image, the radiographing order information and the radiography performance information are related to one another so as to make a radiographing turn correspond to a reading turn, it is possible to relate each information without using identification information of a cassette.

Preferably, in the method of the third aspect of the present invention, the first key information and the second key information include information of at least one of a radiographic part and a radiographic direction.

According to the above-mentioned method, at mamma image radiography, which often requires performing a plurality of times of radiography corresponding to different radiographic parts and different radiographic directions, a radiographic part and/or a radiographic direction, which are/is information especially effective to relate radiographing order information and radiography performance information to each other, can be used as key information.

Preferably, the method of the third aspect of the present invention further comprises: detecting an angle of a radiographic platform to place a subject on, in the mammography apparatus; and determining at least one of the radiographic part and the radiographic direction according to the detected angle, in the mammography apparatus, wherein the transmitting the radiography performance information including the first key information includes transmitting information of the-determined at least one of the radiographic part and the radiographic direction as the first key information to the controller.

According to the above-mentioned method, it is possible to determine a radiographic part and/or a radiographic direction as key information by detecting an angle of a radiographic platform.

Preferably, the method of the third aspect of the present invention-further comprises: detecting an angle of a radiographic platform to place a subject on, in the mammography apparatus; and determining at least one of the radiographic part and the radiographic direction based on information of the detected angle, in the mammography apparatus.

According to the above-mentioned method, it is possible to determine a radiographic part and/or a radiographic direction at the controller according to an angle of the radiographic platform which is detected by the mammography apparatus.

Preferably, the method of the third aspect of the present invention further comprises: inputting information of at least one of the radiographic part and the radiographic direction, in the mammography apparatus, wherein the transmitting the radiography performance information including the first key information includes transmitting the inputted information of at least one of the radiographic part and the radiographic direction as the first key information to the controller.

According to the above-mentioned method, inputted information of a radiographic part and/or a radiographic direction can be used as key information.

Preferably, the method of the third aspect of the present invention further comprises: inputting a radiographing turn of radiography to be performed based on the radiographing order information, in the controller, wherein the transmitting the radiography performance information including the first key information includes transmitting information which indicates a radiographing turn of the mamma image as the first key information to the controller, the storing the radiographing order information includes storing the radiographing order information and the inputted radiographing turn so as to relate the radiographing order information and the radiographing turn to each other, in the storage section of the controller, and the relating the radiography performance information and the radiographing order information to each other includes relating the radiography performance information and the radiographing order information to each other so as to make the radiographing turn included in the radiography performance information correspond to the radiographing turn related to the stored radiographing order information.

More preferably, the method further comprises: transmitting the mamma image read from the cassette from the reading apparatus to the controller, in a reading turn of the mamma image from the cassette; and relating the mamma image, the radiographing order information and the radiography performance information to one another so as to make the radiographing turn of the mamma image correspond to the reading turn of the mamma image, in the controller.

According to the above-mentioned method, based on information of a radiographing turn as key information, and an inputted radiographing turn of radiography to be performed based on radiographing order information, the radiographing order information and radiography performance information are related to each other. Further, a mamma image, the radiographing order information and the radiography performance information are related to one another so as to make a radiographing turn correspond to a reading turn. Therefore, even in the case of continuously performing a plurality of times of radiography with the radiographing turn inputted in advance, it is automatically relate the mamma image, the radiographing order information and the radiography performance information to one another. Therefore, it is not necessary for a radiographic technician to travel to the reading apparatus to insert a cassette, and thereby, it is possible to improve efficiency of a radiography operation.

Preferably, the method of the third aspect of the present invention further comprises: displaying correspondence among the mamma image, the radiographing order information and the radiography performance information that are related to one another, on a display section of the controller.

According to the above-mentioned method, it is possible to easily confirm correspondence among a mamma image, radiographing order information and radiography performance information that are related to one another.

Preferably, the method of the third aspect of the present invention further comprises performing radiography with a part/direction specifier attached to the cassette, the part/direction specifier indicating a radiographic part and a radiographic direction in the mamma image.

According to the above-mentioned method, with the part/direction specifier, it is possible for a radiographic technician to easily determine a radiographic part and a radiographic direction in a radiographed mamma image, and thereby, it is possible to manage mamma images more accurately. Further, since the part/direction specifier is attached to a cassette to be used, it is not necessary to change a structure of the cassette. Therefore, it is possible to easily determine a radiographic part and radiographic direction with cost reduced.

Preferably, the method of the third aspect of the present invention further comprises performing radiography with a part/direction specifier attached to one of the radiographic platform of the mammography apparatus and a pressure plate for compressing a mamma, the part/direction specifier indicating a radiographic part and a radiographic direction in the mamma image.

According to the above-mentioned method, with the part/direction specifier, it is possible for a radiographic technician to easily determine a radiographic part and a radiographic technician in a radiographed mamma image. Therefore, it is possible to manage mamma images more accurately. Further, since the part/direction specifier is attached to either a radiographic platform or a pressure plate to be used, it is not necessary to change a structure of the mammography apparatus. Thereby, it is possible to easily determine a radiographic part and a radiographic direction with cost reduced.

In accordance with a fourth aspect of the present invention, a method for managing information in a mammography system comprising a mammography apparatus for radiographing a mamma image of a patient by irradiating radiations and for reading the mamma image as digital data, and a controller for obtaining the read mamma image from the mammography apparatus, the controller being connected to the mammography apparatus, the method comprises: transmitting radiography performance information including first key information and the read mamma image so as to relate the radiography performance information and the mamma image to each other, from the mammography apparatus to the controller, the first key information for relating the radiography performance information and radiographing order information to each other; storing the radiographing order information including second key information in a storage section of the controller, the second key information for relating the radiography performance information and the radiographing order information; and relating the mamma image, the radiographing order information and the radiography performance information to one another based on the first key information included in the radiography performance information transmitted from the mammography apparatus and the second key information included in the radiographing order information, in the controller.

According to the method of the fourth aspect, since, based on key information, a mamma image and radiography performance information both transmitted from the mammography apparatus for radiographing and reading a mamma image, and radiographing order information are automatically related to one another, it is possible to omit an operation to select radiographing order information to be related to radiography performance information in the controller. Therefore, it is not necessary for a radiographic technician to travel to the controller for the selecting operation, and thereby, at mamma image radiography in particular, which often requires performing a plurality of times of radiography corresponding to different radiographic parts and different radiographic directions, it is possible to improve efficiency of a radiography operation.

In accordance with a fifth aspect of the present invention, a method for managing information in a mammography system comprising a mammography apparatus for radiographing a mamma image of a patient by irradiating radiations and for recording the mamma image in a cassette, a reading apparatus for reading the mamma image from the cassette, and a controller for storing radiographing order information including second key information for relating radiography performance information and the radiographing order information and for obtaining the read mamma image by controlling the reading apparatus, when a plurality of mamma images corresponding to one patient are radiographed by using a plurality of cassettes, at each time of radiographing one of the plurality of mamma images in the mammography apparatus, the method comprises: transmitting the radiography performance information including first key information, from the mammography apparatus to the controller, the first key information for relating the radiography performance information and radiographing order information to each other; and relating the obtained mamma image, the radiographing order information and the radiography performance information to one another based on the first key information included in the radiography performance information transmitted from the mammography apparatus and the second key information included in the radiographing order information, in the controller.

According to the method of the fifth aspect, since a mamma image, radiographing order information and radiography performance information are automatically related to one another at each time of radiographing one mamma image, it is possible to securely relate those information without cassette registration performed. Therefore, at mamma image radiography in particular, which often requires performing a plurality of times of radiography corresponding to different radiographic parts and different radiographic directions, it is possible to improve efficiency of a radiography operation. Further, since reading a mamma image is performed at each time of radiography, there is no necessity of, for example, a radiographic technician memorizing which cassette records a mamma image of which radiographic part and which radiographic direction, and thereby, it is possible to reduce a burden of the radiography operation by the radiographic technician. Further, it is possible to omit an operation to select radiographing order information to be related to radiography performance information in the controller. Therefore, it is not necessary for a radiographic technician to travel to the controller for the selecting operation, and at mamma image radiography in particular, which often requires performing a plurality of times of radiography corresponding to different radiographic parts and different radiographic directions, it is possible to improve efficiency of a radiography operation.

BRIEF DESCRIPTION OF THE DRAWINGS

The present invention will become more fully understood from the detailed description given hereinafter and the accompanying drawing given by way of illustration only, and thus are not intended as a definition of the limits of the present invention, and wherein:

FIG. 6 is a view showing a data structure example of an order file;

FIG. 7 is a flowchart illustrating a first radiography process executed in the mammography system in the first embodiment;

FIG. 8 is a flowchart describing correspondence among a mamma image, radiographing order information and radiography performance information in the first radiography process;

FIG. 12A is a view showing a placement example of the part/direction specifier to a cassette; FIG. 12B is a view showing a left mamma image radiographed in an in-out direction with the part/direction specifier placed; FIG. 12C is a view showing a right mamma image radiographed in an in-out direction with the part/direction specifier placed;

FIG. 13 is a flowchart illustrating a second radiography process executed in the mammography system in the second embodiment;

FIGS. 15A to 15D are views showing an example of determining a radiographic part/direction in a mamma image radiographed with the use of lead plates.

EMBODIMENTS OF THE INVENTION

Hereinafter, embodiments according to the present invention will be described with reference to figures.

[First Embodiment]

In the first embodiment, described is an example in which radiographing order information and radiography performance information are related to each other with information of a radiographic part and a radiographic direction (hereafter, it is referred to as radiographic part/direction) included in the radiography performance information as key information, and based on a cassette ID related to the radiographing order information and a cassette ID related to a radiographed mamma image, the mamma image, the radiographing order information and the radiography performance information are automatically related to one another.

First, a structure will be described.

Figure 1:
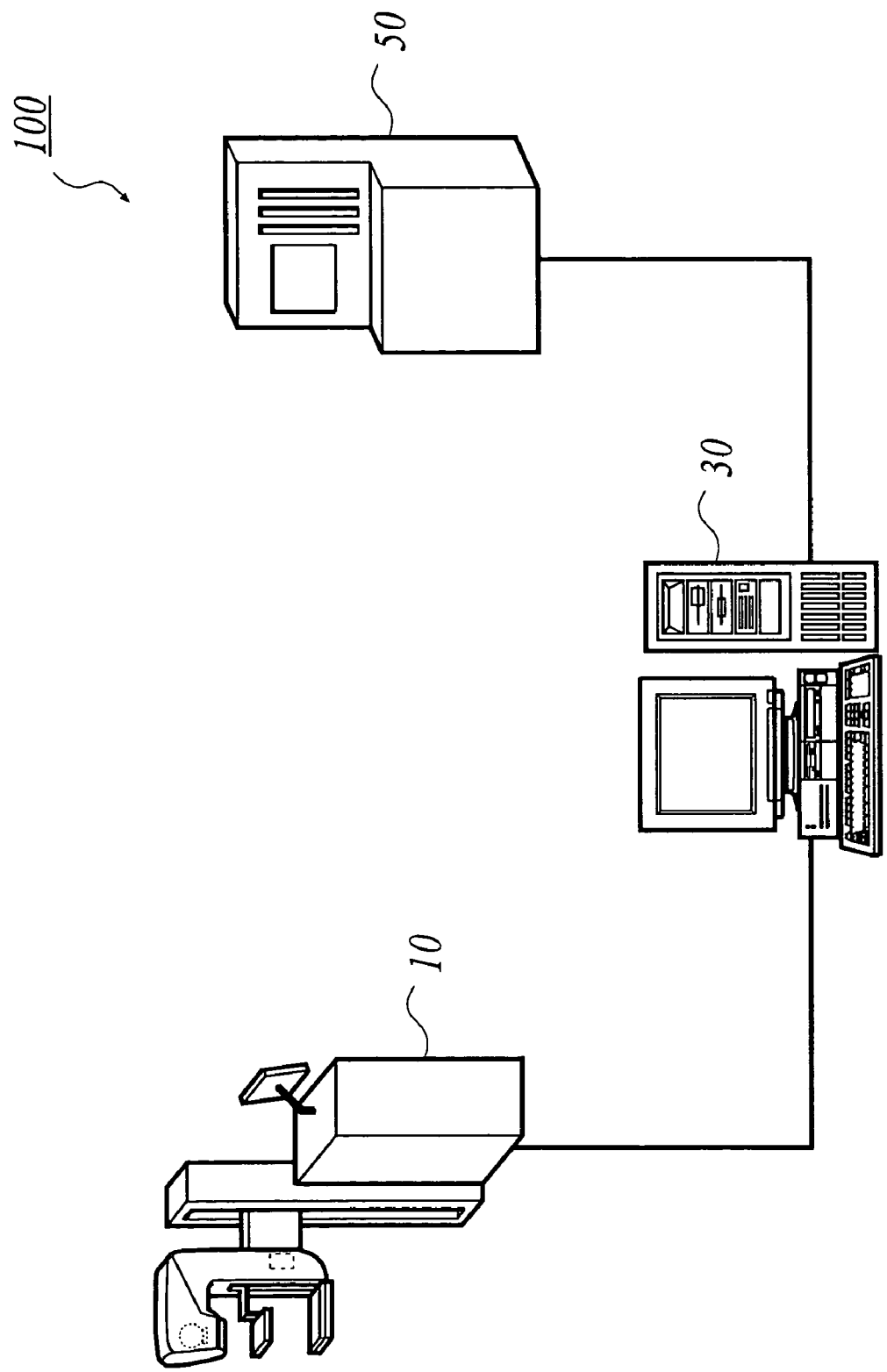
FIG. 1 is a system structure of a mammography system in an embodiment to which the present invention is applied.

FIG. 1 shows a system structure of a mammography system 100 in the present embodiment.

As shown in FIG. 1, the mammography system 100 comprises a mammography apparatus 10, a controller 30, and reading apparatus 50. The mammography apparatus 10 and the reading apparatus 50 are connected to the controller 30 so that they are capable of transmitting information to each other.

The mammography apparatus 10 is used to radiograph a radiation image of mamma by irradiating radiations to the mamma of a patient as a subject. In the present embodiment, a radiographing apparatus of a type which performs radiography with a cassette will be described as an example.

Figure 2:
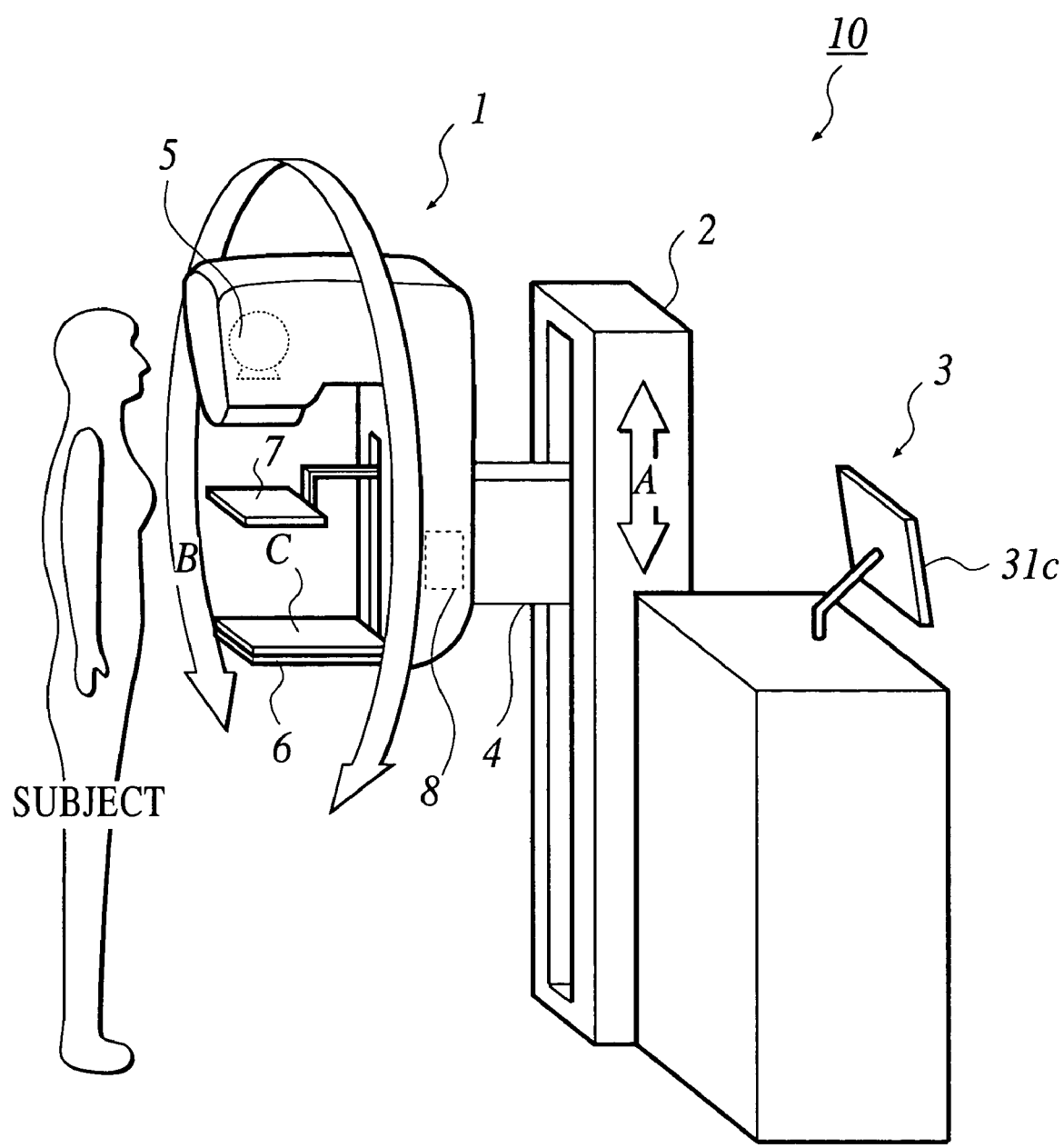
FIG. 2 is an external view of a mammography apparatus.

FIG. 2 shows the mammography apparatus 10.

As shown in FIG. 2, the mammography apparatus 10 comprises a radiographing unit 1 for performing radiography by irradiating radiations, a supporting pole 2, and a main unit 3. The radiographing unit 1 is placed movably along the supporting pole 2 (movably in a direction indicated by an arrow A) so as to be adjusted to a height of patient's mamma, and also placed rotatably with a supporting shaft 4 as its shaft (rotatably in a direction indicated by an arrow B) so as to change a radiographic direction. The rotation can be made manually by a radiographic technician, or can be made by operating the main unit 3.

The radiographing unit 1 comprises a radiation source 5 for generating radiations and a radiographic platform 6 for placing mamma, where the radiation source 5 and the radiographic platform 6 face each other, and a pressure plate for pressing mamma by compressing the mamma placed on the radiographic platform 6. The radiographic platform 6 comprises a cassette holder (not shown) for fixing a cassette c, and thereby it is possible to attach the cassette c at the upper part of the radiographic platform 6. The cassette c is used to absorb radiations transmitted through a subject within a phosphor plate incorporated therein, and to record the radiation image.

In addition, within the radiographing unit 1, placed is an angle detecting unit 8 for detecting a rotation angle of the radiographing unit 1 being rotated with the supporting shaft 4 as a rotation shaft. The angle detecting unit 8 outputs information of the rotation angle detected at the time of radiography, to the main unit 3. In other words, by the angle detecting unit 8 detecting a rotation angle of the radiographic platform 6, it is possible to achieve an angle detecting section.

Next, with reference to FIG. 3, an internal structure of the main unit 3 will be described.

Figure 3:
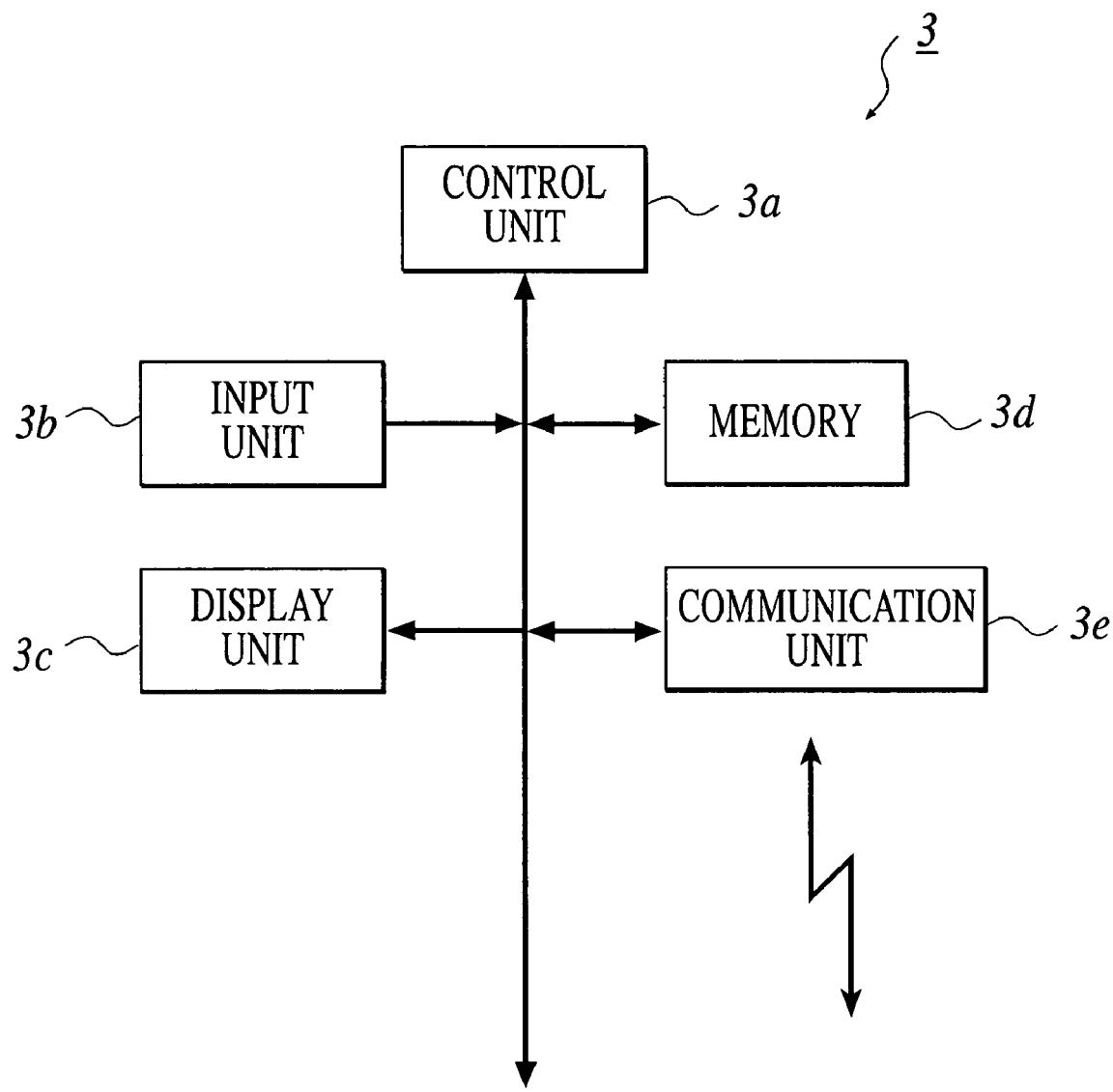
FIG. 3 is a functional structure of a main unit.

As shown in FIG. 3, the main unit 3 comprises a control unit 3a, an input unit 3b, a display unit 3c, a memory 3d and a communication unit 3e.

The control unit 3a comprises a CPU (Central Processing Unit) and the like, loads a radiography program and a first radiography processing program according to the present invention, and integrally controls a radiography operation of each unit of the mammography apparatus 10 in cooperation with the programs loaded from the memory 3d, the radiography operation such as adjusting radiation irradiation timing and irradiation amount in the radiation source 5, rotation control of the radiographing unit 1, and the like. Further, when information of a rotation angle of the radiographing unit 1 is inputted at the angle detecting unit 8, the control unit 3a determines a radiographic part/direction based on the information of a rotation angle.

Figure 4A:
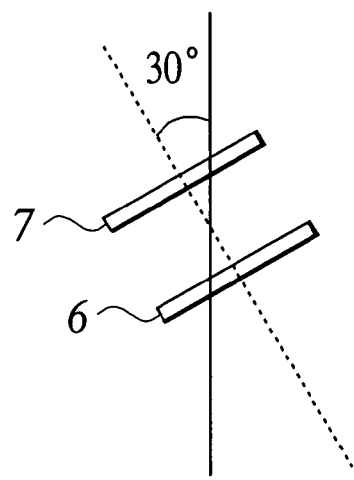
FIGS. 4A and 4B are views showing an example of determining a radiographic part/direction according to detected angle information of a radiographing unit.
Figure 4B:
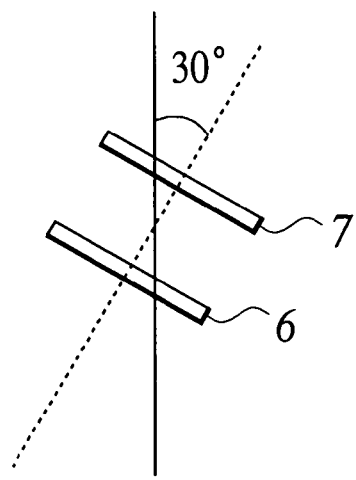

With reference to FIGS. 4A and 4B, an example of determining a radiographic part/direction will be described. FIGS. 4A and 4B are views showing the pressure plate 7 and the radiographic platform 6 seen from a subject side. As shown in FIG. 4A, with an angle at a home position where the radiographing unit 1 is not rotated defined as 0 degree, for example, if the radiographing unit 1 is rotated from the home position as much as 30 degree counterclockwise in order to perform radiography on a left mamma in an oblique direction, a rotation angle is detected as "−30 degree". Further, as shown in FIG. 4B, for example, if the radiographing unit 1 is rotated from the home position as much as 30 degree clockwise in order to perform radiography on a right mamma in an oblique direction, a rotation angle is detected as "+30 degree". In other words, if a sign of the detected rotation angle is "+", a radiographic part is determined as a left mamma, and if a sign of the detected rotation angle is "−", a radiographic part is determined as a right mamma. In addition, if a rotation angle is within 0 to 15 degree from the home position, a radiographic direction is determined as an up-down direction, if a rotation angle is within 15 to 75 degree from the home position, a radiographic direction is determined as an oblique direction, and if a rotation angle is within 75 to 90 from the home position, a radiographic direction is determined as an in-out direction. In other words, by determining a radiographic part and/or a radiographic direction in the control unit 3a, it is possible to achieve a determination section.

In a first radiography process, after radiography is performed, the control unit 3a transmits various types of information in regard to a performance result of the radiography as radiography performance information, to the controller 30 through the communication unit 3e, the various types of information such as a tube voltage (unit; kV) in the radiation source 5, a tube current (unit; mA) value, radiation irradiation amount (indicated by product of the tube current value and irradiation time (second), unit; mAs), compression amount by the pressure plate 7 (indicated by moving distance of the pressure plate 7, unit; mm), a radiographic part/direction (indicated by a character code, the following codes indicates a radiographic direction, CC; up-down direction, M; in-out direction, and MLO; oblique direction) and the like.

The input unit 3b comprises keys to input various types of radiographing conditions, and outputs an operation signal corresponding to an operated key to the control unit 3a. For example, the input unit 3b comprises various keys such as numeric keys to input a tube voltage, a tube current value and a rotation angle of the radiographing unit 1, and the like.

Here, the input unit 3b may comprise a radiographic part key to input information of a radiographic part whether a left mamma or a right mamma has been radiographed, a radiographic direction key to input a rotation angle of the radiographing unit 1, and the like. The radiographic direction key comprises keys corresponding each radiographic direction, an up-down direction, an in-out direction and an oblique direction. For example, when a key of the in-out direction key is pushed, the radiographing unit 1 is automatically rotated to a rotation angle for radiographing in an in-out direction. If the input unit 3b comprises the radiographic direction key, the radiography performance information includes a radiographic direction indicated by the pushed radiographic direction key. In other words, by inputting information of a radiographic part/direction with operating the input unit 3b, it is possible to achieve a part/direction input section. Alternatively, by inputting left/right information indicating whether a radiographic part is a right mamma or a left mamma with operating the input unit 3b, it is possible to achieve a left/right information input section.

The display unit 3c, as shown in FIG. 2, comprises a display 31c composed of an LCD (Liquid Crystal Display) and the like, and displays various display information such as a processing result by the control unit 3a and the like on the display 31c.

The memory 3d comprises a RAM (Random Access Memory) and a ROM (Read Only Memory), and stores various types of programs such as a radiography program of a mamma image, a first radiography process according to the present invention, and the like. In addition, the memory 3d temporarily stores the processing result by the control unit 3a, and stores various types of information such as the radiography performance information and the like.

The communication unit 3c comprises a communication interface such as a Network Interface Card (hereinafter, it is referred to as NIC), a modem or the like. In other words, by being connected to the controller 30 to transmit the radiography performance information including key information after radiography is performed, it is possible to achieve a communication section.

Next, the controller 30 will be described.

Figure 5:
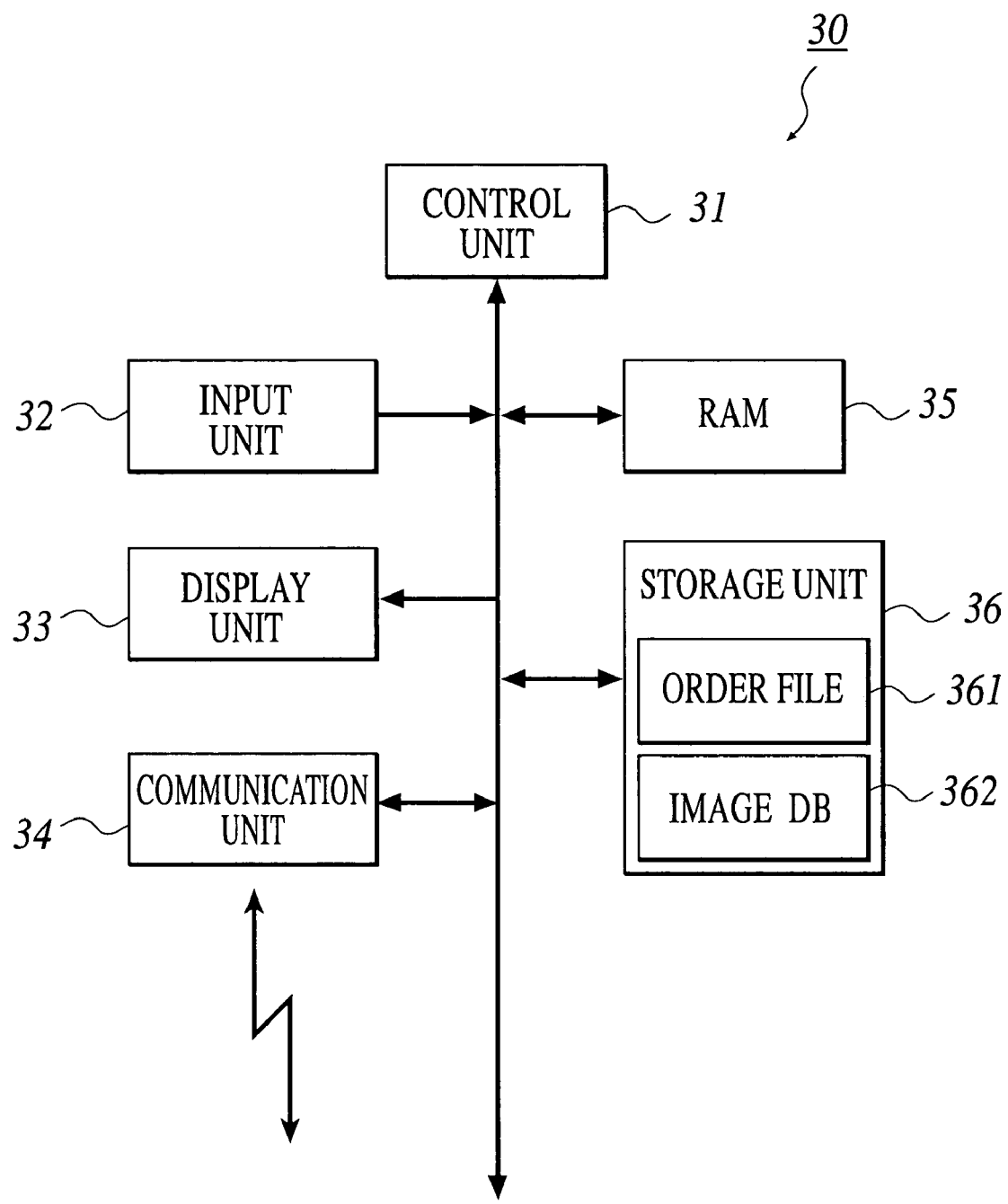
FIG. 5 is a functional structure of a controller.

FIG. 5 shows a functional structure of the controller 30.

As shown in FIG. 5, the controller 30 comprises a control unit 31, an input unit 32, a display unit 33, a communication unit 34, a RAM 35 and a storage unit 36.

The control unit 31 comprises a CPU and the like. The control unit 31 develops a system program, a first radiography processing program (see FIG. 7) according to present invention and the like stored in the storage unit 36, into the RAM 35, and integrally controls a processing operation in cooperation with the programs.

In the first radiography process, based on information of a radiographic part/direction included in the radiography performance information transmitted from the mammography apparatus 10 and information of a radiographic part/direction included in radiographing order information of a selected patient, the control unit 31 relates the radiography performance information to the radiographing order information and stores them in an order file 361. Further, when a cassette ID is inputted at the input unit 32, the control unit 31 relates the cassette ID to the radiographing order information and stores them in the order file 361. Further, when a mamma image and a cassette ID related to the mamma image are transmitted from the reading apparatus 50, the control unit 31 relates the radiographing order information and the radiography performance information to the mamma image based on the cassette ID. In other words, by relating a mamma image, radiographing order information and radiography performance information to one another in the control unit 31, it is possible to achieve a control section.

The input unit 32 comprises a keyboard including numeric keys, character keys and various types of function keys, and a touch panel integrally structured with the display unit 33. The input unit 32 outputs an operation signal corresponding to an operated key, to the control unit 31. In other words, by inputting a cassette ID with operating the input unit 32, it is possible to achieve an identification information input section. Here, with the cassette ID barcoded and placed with the cassette c, the controller 30 may comprises a barcode reader to input a cassette ID.

The display unit 34 comprises an LCD, a CRT (Cathode Ray Tube) or the like, and displays various types of operation screens and various types of display information such as a processing result by the control unit 31. In other words, by displaying a confirmation screen (see FIG. 9) for confirming correspondence among a mamma image, radiographing order information and radiography performance information on the display unit 34, it is possible to achieve a display section.

The communication unit 34 comprises an NIC, a modem or the like, and transmits/receives information with an external device. For example, before radiography is performed, the communication unit 34 receives radiographing order information from HIS or RIS (not shown), and after radiography is performed, the communication unit 34 receives radiography performance information from the mammography apparatus 10 and also receives a mamma image and a cassette ID related to the mamma image from the reading apparatus 50.

The RAM 35 forms a work area for temporarily storing various types of programs executed by the control unit 31 and data regarding the programs.

The storage unit 36 comprises a magnetic storage medium, an optical storage medium or a semiconductor memory, and stores a system program, a first radiography processing program, data processed by each program and the like.

In addition, the storage unit 36 is a storage section for storing radiographing order information including key information, and comprises the order file 361 for storing the radiographing order information updatably. As shown in FIG. 6, in the order file 361, radiographing order information is stored at each identification information (hereinafter, it is referred to as order ID) for individually identifying the radiographing order information. Radiographing order information includes information regarding a patient (hereinafter, it is referred to as patient information) such as a patient ID of a patient of a radiography subject, a name of the same and the like, information regarding radiography (hereinafter, it is referred to as radiography information) such as a radiographic part/direction, radiography date and the like. Further, each radiographing order information is related to a cassette ID of a cassette used in radiography corresponding to the radiographing order information, and also related to radiography performance information.

Next, the reading apparatus 50 will be described.

The reading apparatus 50 is used to read a mamma image recorded in a cassette c. The reading apparatus 50 comprises a communication section (not shown) such as an NIC, a modem or the like. The reading apparatus 50 reads a medical image and a cassette ID from a cassette c, and transmits the read medical image with the cassette ID related to, to the controller 40.

Next, an operation in the first embodiment will be described.

In the first embodiment, described is an example in which radiographing order information and radiography performance information are related to each other with a radiographic part/direction as key information, and the radiographing order information and a mamma image are related to each other based on a cassette ID.

With reference to FIG. 7, a first radiography process performed in the mammography system 100 will be described. Here, normally at the time of radiographing mamma images, more than one time of radiography at the same part/direction are not performed. Therefore, in the present embodiment, if there are a plurality of pieces of radiographing order information for one patient, it is assumed that all the radiographic parts/directions in each radiographing order information are different from one another.

In the first radiography process shown in FIG. 7, the controller 30 displays a list of patients who are scheduled to be radiographed on the display unit 33 based on. radiographing order information stored in the order file 361. When a radiographic technician selects and inputs a patient of a radiography subject among the list-displayed patients at the input unit 32, the controller 30 displays radiographing order information corresponding to the selected patient in a list form (Step S1).

Next, in Step S2, cassette registration of a cassette c to be used for radiography is performed. First, when the radiographic technician inputs a cassette ID of the cassette c to be used for radiography at the input unit 42 to the controller 30, the controller 30 stores the list-displayed pieces of radiographing order information with the inputted cassette ID related to in the order file 361, in the turn from a piece of radiographing order information displayed at the top of the list. Here, the following description will be made with the assumption that the selected patient is related to four different pieces of radiographing order information, whose radiographic parts/directions are a left mamma in an up-down direction, a left mamma in an in-out direction, a right mamma in an up-down direction, and a right mamma in an in-out direction, and that cassette registration corresponding to the four times of radiography is performed at once.

Next, the radiographic technician travels with a plurality of cassettes c on which cassette registration is performed, to a radiographic room where the mammography apparatus 10 is installed, and set a cassette c corresponding to a radiographic part/direction to be radiographed at among the plurality of cassettes, in the mammography apparatus 10. Then, the radiographic technician inputs a radiography instruction. In the mammography apparatus 10, radiations are irradiated according to the radiography instruction for performing radiography (Step S3). In accordance with the above-described example, since cassette registration corresponding to four times of radiography according to four different radiographic parts/directions is performed, the four times of radiography are continuously performed with a corresponding cassette c exchanged to be used at each time of changing a radiographic part/direction.

The mammography apparatus 10 generates at each time of performing radiography, radiography performance information with information of a radiographic part/direction as key information. Then, the mammography apparatus 10 transmits the radiography performance information including the information of a radiographic part/direction to the controller 30 (Step S4). When receiving the radiography performance information, the controller 30 relates radiographing order information to the radiography performance information based on the information of a radiographic part/direction included in the radiographing order information of the selected patient, and stores them in the order file 361 (Step S5).

For example, as shown in FIG. 8, when there are pieces of radiographing order information corresponding to different radiographic parts/directions, which are A (radiographic part/direction; RCC), B (radiographic part/direction; RM), C (radiographic part/direction; LCC) and D (radiographic part/direction; LM), and if radiography in the mammography apparatus 10 is performed in the turn of RM, RCC, LCC and LM, pieces of radiography performance information W, X, Y and Z including information of each radiographic part/direction are transmitted to the controller 30 in the radiographing turn. Then, the controller 30 sequentially relates the radiographing order information B and the radiography performance information W, the radiographing order information A and the radiography performance information X, the radiographing order information C and the radiography performance information Y, and the radiographing order information D and the radiography performance information Z, so as to correspond a radiographic part/direction.

When radiography is completed, the radiographic technician travels to the reading apparatus 50 with cassettes c which have completed the radiography. Then, the radiographic technician sequentially sets the cassettes c to the reading apparatus 50, and inputs a reading instruction. Then, the reading apparatus 50 reads mamma images and cassette IDs from the cassettes c (Step S5). The read cassette ID is written in a header area of the mamma image, and thereby the cassette ID is related to the mamma image. Then, the mamma images related to the cassette ID are transmitted from the reading apparatus 50 to the controller 30 in the turn of having been read by the reading apparatus 50.

When the controller 30 receives a mamma image from the reading apparatus 50 and stores the received mamma image in the image DB 362, the controller 30 reads a cassette ID from the header area of the received mamma image, and relates the mamma image, radiographing order information and radiography performance information to one another based on the read cassette ID and the cassette ID related to the radiographing order information (Step S8).

For example, as shown in FIG. 8, when the controller 30 relates a cassette ID 10101 to the radiographing order information A, a cassette ID 10102 to the radiographing order information B, a cassette ID 10103 to the radiographing order information C and a cassette ID 10104 to the radiographing order information D, and when the reading apparatus 50 relates the cassette ID 10102 to a data file of a mamma image mam1.jpg, the cassette ID 10103 to a mamma image mam2.jpg, the cassette ID 10101 to a mamma image mam3.jpg and the cassette ID 10104 to a mamma image mam4.jpg, the mamma image mam1.jpg is related to the radiographing order information B and the radiography performance information W, the mamma image mam2.jpg is related to the radiographing order information C and the radiography performance information Y, the mamma image mam3.jpg is related to the radiographing order information A and the radiography performance information X, and the mamma image mam4.jpg is related to the radiographing order information D and the radiography performance information Z.

In other words, when a plurality of times of radiography are to be performed on one patient, and radiographic parts/directions of the plurality of times of radiography are all different from one another, it is possible to continuously perform the plurality of times of radiography by at once performing cassette registration corresponding to the plurality of times of radiography.

When the reading apparatus 50 completes reading the cassettes c, the radiographic technician goes back to the operation of the controller 30. When the controller 30 completes relating a mamma image, radiographing order information and radiography performance information to one another, the controller 30 displays a confirmation screen 331 (see FIG. 9) on the display unit 33, the confirmation screen 331 for confirming the related mamma image, the related radiographing order information and the related radiography performance information, and correspondence is confirmed (Step S9).

Figure 9:
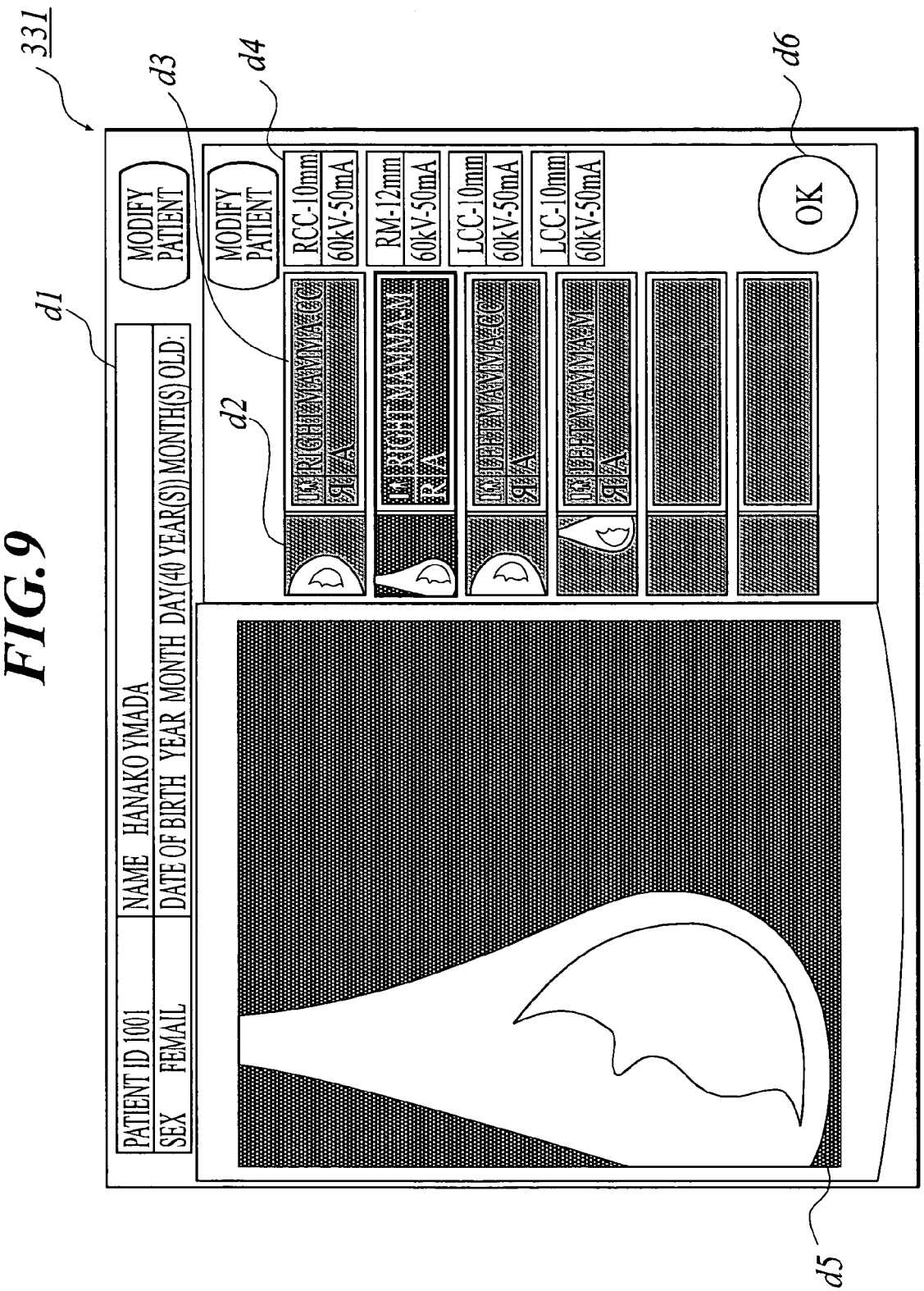
FIG. 9 is a confirmation screen for confirming correspondence among a mamma image, radiographing order information and radiography performance information.

As shown in FIG. 9, in the confirmation screen 331, patient information d1 of a radiographed patient is displayed at the upper part of the screen, and at the right part of the screen, a thumbnail image d2 of a radiographed mamma, radiographing order information d3 of the patient and radiographing performance information d4 are displayed with being related to one another. If radiographing order information to which the radiographic technician desires to display an enlarged image of a thumbnail mamma image corresponding to, is selected among the displayed radiographing order information, a mamma image d5 corresponding to the selected radiographing order information is displayed in a display area at the left part of the screen.

In the above-mentioned confirmation screen 331, the radiographic technician looks at a radiographed mamma image and according to its radiographic part/direction, confirms correspondence among a mamma image, radiographing order information and radiography performance information. If the correspondence is adequate, the radiographic technician pushes an OK button d6 displayed at the lower part of the screen.

Figure 10A:
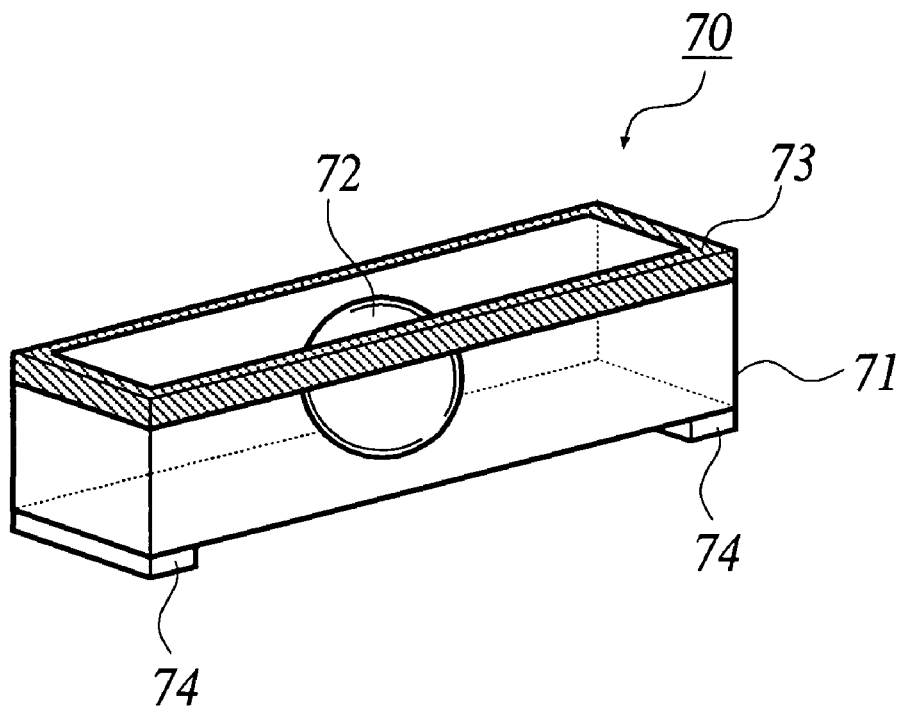
FIG. 10A is a view showing one example of a part/direction specifier for making it easy to determine a radiographic part/direction in a mamma image.

At this time, in order for the radiographic technician to easily distinguish a radiographic part/direction of a displayed mamma image, a part/direction specifier as shown in FIG. 10A may be used at the time of radiography. As shown in FIG. 10A, the part/direction specifier has a structure in which a metal sphere 72 made of radiation absorbable material such as lead or the like is provided within a prism-like case 71 made of radiation transmittable material such as plastic or the like, so as to enable the metal sphere 72 to smoothly move from one edge to another of the case 71. Further, a frame 73 forms the fringe of the upper surface of the case 71. The frame 73 is made of radiation absorbable material such as lead or the like.

Further, an adhesive tape 74 adheres to the bottom part of the case 71, the adhesive tape 74 for attaching the part/direction speficier 70 to the cassette c, the radiographic platform 6 or the pressure plate 7. Here, as long as it is possible to attach and detach the part/direction specifier, it is not limited to the adhesive tape, and another member such as a sticky tape or the like may be applied. Therefore, its detailed structure is not in particular limited.

At the time of radiography, according to a radiographic part/direction, by attaching the above-mentioned part/direction specifier 70 to a cassette c to be used for the radiography, the radiographic platform 6 of the mammography apparatus 10, or the pressure plate 7 of the same, it is possible to easily distinguish a radiographic part/direction of a radiographed image. An example of distinguishing a radiographic part/direction with the use of the part/direction specifier 70 will be described with reference to FIGS. 11A to 11C, and FIGS. 12A to 12C.

First, with reference to FIGS. 11A to 11C, a case of radiographing in an up-down direction (CC) will be described. Here, a case in which the part/direction specifier 70 is attached on the upper surface of a cassette c will be described.

Figure 11A:
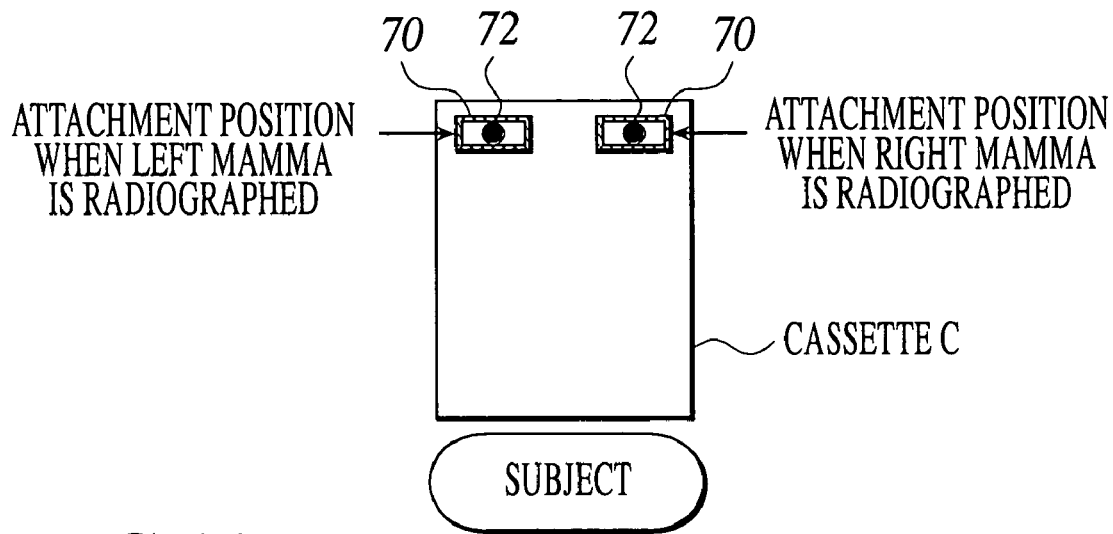
FIG. 11A is a view showing a placement example of the part/direction specifier to a cassette.

FIG. 11A shows a state where a cassette c is set to the radiographic platform 6 before radiography is performed. When the part/direction specifier 70 is attached to a position on the cassette c, the position facing a subject M side, if a left mamma is to be radiographed, the part/direction specifier 70 is attached to the left side seen from the subject side, and if a right mamma is to be radiographed, the part/direction specifier 70 is attached to the right side seen from the subject side.

Figure 11B:
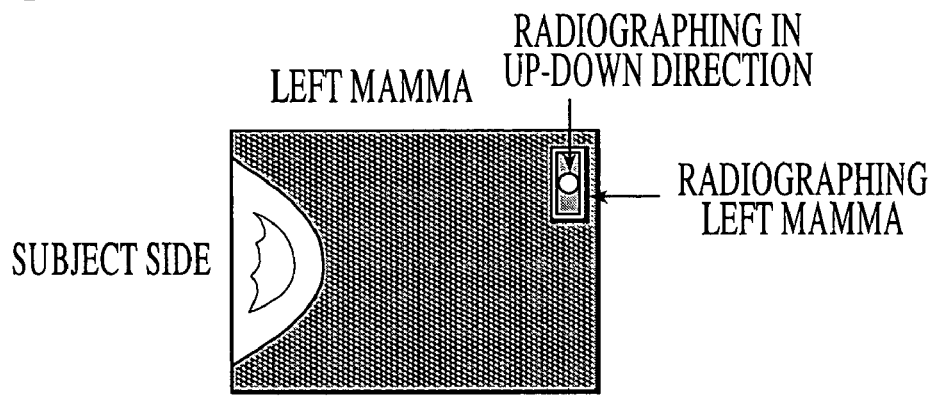
FIG. 11B is a view showing a left mamma image radiographed in an up-down direction with the part/direction specifier placed.
Figure 11C:
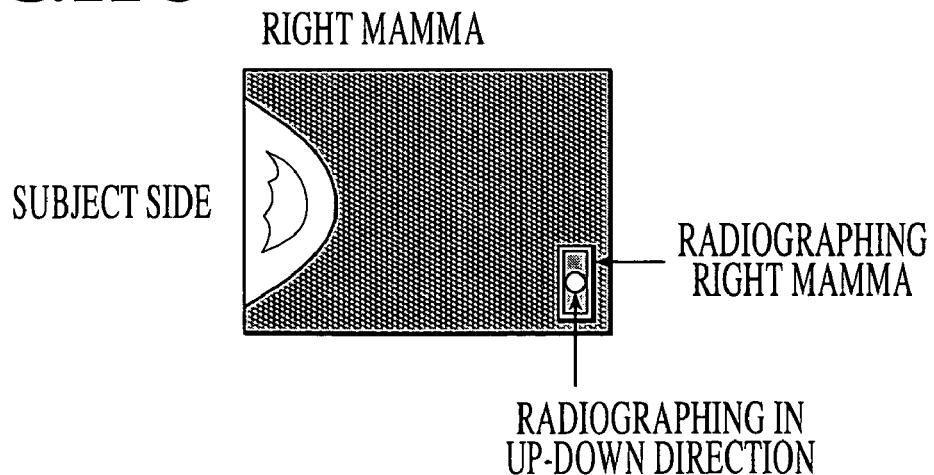
FIG. 11C is a view showing a right mamma image radiographed in an up-down direction with the part/direction specifier placed.

When radiography is performed in this state, in the case of radiographing a left mamma, a left mamma image as shown in FIG. 11B is obtained, and in the case of radiographing a right mamma, a right mamma image as shown in FIG. 11C is obtained. In each image, an area where the metal sphere 72 and the frame 73 made of radiation absorbable material are radiographed has low density, and an area where the case 71 made of radiation transmittable material has high density.

Since two images shown in FIG. 11B and FIG. 11C have a similar shape of a subject, it is not possible to distinguish at a glance whether radiographed image is a right mamma or a left mamma. However, with the use of the part/direction specifier 70, as shown in FIG. 11B, assuming a subject image area side of a radiographed image as a subject side, since the part/direction specifier 70 is attached at the left side of the cassette c seen from the subject side in a left mamma image, it is possible to easily distinguish that a radiographic part is a left mamma. Further, since the metal sphere 72 of the part/direction specifier is located approximately at the center of the frame, it is estimated that the radiography has been performed in a state in which the cassette c is approximately horizontally positioned. Thereby, it is possible to distinguish that a radiographic direction is an up-down direction.

Similarly, in regard to a right mamma image shown in FIG. 11C as well, since the part/direction specifier is attached to the right side of the cassette c seen from the subject side, it is possible to easily distinguish that a radiographic part is a right mamma. Further, according to the location of the metal sphere 72 of the part/direction specifier 70, it is possible to distinguish that a radiographic direction is an up-down direction.

Next, with reference to FIGS. 12A to 12C, a case of radiographing in an in-out direction (M) will be described.

FIG. 12A shows a state where a cassette c is set to the radiographic platform 6 before radiography is performed. In the case of an in-out direction, as well as the case of an up-down direction, when the part/direction specifier 70 is attached to a position on the cassette c, the position facing a subject M side, if a left mamma is to be radiographed, the part/direction specifier 70 is attached to the left side seen from the subject side, and if a right mamma is to be radiographed, the part/direction specifier 70 is attached to the right side seen from the subject side.

After the part/direction specifier 70 is attached to a cassette c according to a radiographic part/direction, and then radiography is performed with the radiographing unit 1 rotated according to the radiographic part/direction, if a left mamma is radiographed, a left mamma image shown in FIG. 12B is obtained, and if a right mamma is radiographed, a right mamma image shown in FIG. 12C is obtained. Since only the difference between the two images shown in FIGS. 12B and 12C is a position of a radiographed image, it is not possible to distinguish at a glance whether a radiographed image is a right mamma or a left mamma. However, as well as the case of an up-down direction, with the use of the part/direction specifier 70, in a left mamma image shown in FIG. 12B, since the part/direction specifier 70 is attached to the left side seen from the subject side, it is possible to easily distinguish that a radiographic part is a left mamma. Further, since the metal sphere 72 of the part/direction specifier 70 is located at the edge part, it is estimated that radiography has been performed with the cassette c vertically positioned. Thereby, it is possible to distinguish that a radiographic direction is an in-out direction.

Similarly, in regard to a right mamma image shown in FIG. 12C, since the part/direction specifier 70 is attached to the right side of the cassette c seen from the subject side, it is possible to easily distinguish that a radiographic part is a right mamma. Further, according to a location of the metal sphere 72 of the part/direction specifier 70, it is possible to distinguish that a radiographic direction is an in-out direction.

Figure 10B:
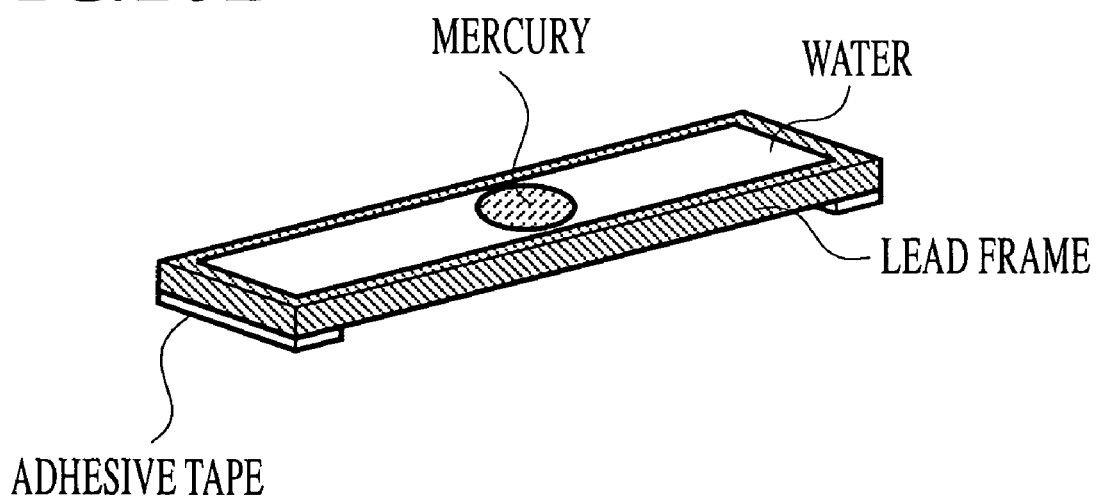
FIG. 10B is a view showing another structure example of a part/direction specifier.

Here, the part/direction specifier 70 shown in FIG. 10A is one example, and as long as an object made of radiation absorbable material is structured so as to smoothly move according to a radiographic direction, the object is not limited to the above-mentioned example. For example, as shown in FIG. 10B, an object having a structure where a approximately rectangular case includes mercury therein so as to enable the mercury to move from one edge to another with water as a medium may be used.

Further, described is the example of the part/direction specifier 70 attached to the cassette c. However, the part/direction specifier 70 may be attached to a back surface of the radiographic platform 6 or an upper surface of the pressure plate 7 for distinguishing a radiographic part/direction of a mamma image.

In this way, when the part/direction specifier 70 is used, on the confirmation screen 331 displayed by the controller 30, mamma images radiographed together with the part/direction specifier 70 are displayed as shown in FIGS. 11B, 11C, 12B and 12C. From the displayed mamma image on the confirmation screen 331, it is possible for a radiographic technician to distinguish a radiographic part/direction. Thereby, it is possible to easily confirm correspondence among a mamma image, radiographing order information and radiography performance information. As is often the case with radiographing a mamma image, radiography is performed on left and right mammas in a plurality of directions. Therefore, in particular, distinguishing a radiographic part/direction with the use of the part/direction specifier 70 is effective, and thereby it is possible to prevent the mix-up of mamma images.

Next, when the OK button d6 is pushed on the confirmation screen 331, the controller 30 re-displays a selection screen of a patient of a next radiography subject on the display unit 33. If it is necessary to advance to radiography on a next patient, a radiographic technician selects a patient of a radiography subject on the selection screen of a patient. If it is necessary to finish radiography, the radiographic technician inputs an instruction of finishing radiography.

In Step S10, the controller 30 determines whether a patient to be radiographed next has been selected. If a patient has been selected (Step S10; Y), the present process returns to Step S2 and perform radiography on the selected patient repeatedly. If a patient has not been selected (Step S10; N), the present process is finished. After the process is finished, a mamma image is stored in a database for storing images, and radiographing order information related to the mamma image, and radiography performance information related to the same are stored as accompanying information of the mamma image in a predetermined database.

As mentioned, by relating radiographing order information and radiography performance information to each other with information of a radiographic part/direction as key information, and by relating the radiographing order information and a radiographed mamma image to each other based on a cassette ID, the mamma image, the radiographing order information and the radiography performance information are related to one another. Therefore, it is possible to omit a selecting operation for selecting radiographing order information which is to be related to radiography performance information by a radiographic technician at the time of radiography, and thereby it is possible to improve efficiency of a radiography operation.

In general, in a group examination or the like, two images of left and right mammas in an oblique direction are radiographed most of the time. In this case, if it is possible to at least distinguish whether a left mamma or a right mamma has been radiographed according to rotation angle information of the radiographing unit 1, since it is possible to automatically relate radiographing order information and radiography performance information, it is especially effective.

Further, since radiographing order information and a mamma image are related to each other based on a cassette ID, if all the radiographic parts/directions at which a plurality of times of radiography are to be performed to the same patient are different from one another, it is possible to continuously perform the plurality of times of radiography. Thereby, since a radiographic technician only has to travel to the controller, to the mammography apparatus and to the reading apparatus once at each time during radiography operation, it is possible to reduce a burden of the radiography operation by the radiographic technician.

Further, if the part/direction specifier 70 is used at the time of radiography, since it is possible to easily distinguish a radiographic part/direction according to a radiographed mamma image, a radiographic technician can easily confirm correspondence among a mamma image, radiographing order information and radiography performance information, each related to one another by the controller 30. Further, since the part/direction specifier 70 is structured to be attachable and detachable, without changing structures of a cassette c and the mammography apparatus 30, it is possible to easily distinguish a radiographic part/direction. Thereby, it is possible to improve efficiency with cost reduced.

Here, the described contents in the present embodiment are a suitable example of the mammography system 100 to which the present invention is applied, and the present invention is not limited to the example.

Described above is the example of relating a mamma image, radiographing order information and radiography performance information to one another under the assumption that all the radiographic parts/directions at which a plurality of times of radiography are performed to the same patient are different from one another. However, for example, if a plurality of times of radiography on the same patient include a plurality of time of radiography at the same radiographic part/direction, radiography operation is performed in a workflow in which the controller 30 performs cassette registration for one group of radiography, the mammography apparatus 10 performs radiography once, and immediately the reading apparatus 50 reads an image. Thereby, even if a plurality of times of radiography at the same radiographic part/direction are included, the controller 40 automatically relates each information and thereby it is possible to omit a selecting operation of radiographing order information to be related with radiography performance information.

Further, described above is the example of performing cassette registration as pre-registration. However, cassette registration may be performed as post-registration. In the case of the post-registration, after a patient of a radiography subject is selected, the mammography apparatus 10 performs radiography without cassette registration performed, and after the reading apparatus 50 completes reading an image, cassette registration is performed in the controller 30. In the controller 30, as well as the case of pre-registration, a cassette ID is related to radiographing order information that is the top one among pieces of radiographing order information of the selected patient.

Further, a barcode reader may be placed on the radiographic platform 6 of the mammography apparatus 10 in order to read a cassette ID provided with a cassette c when the cassette c is attached to the radiographic platform 6 at the time of radiography, and to input the read cassette ID to the mammography apparatus 10. The mammography apparatus 10 relates the inputted cassette ID and radiography performance information to each other and transmits them to the controller 30. Thereby, in the controller 30, it is possible to relate the radiography performance information transmitted from the mammography apparatus 10 and a mamma image transmitted from the reading apparatus 50 to each other directly based on the cassette ID.

Further, if the angle detecting unit 8 is not provided in the mammography apparatus 10, a radiographic technician may input information of a radiographic part/direction at the input unit 32 at each time of radiography.

And so forth, the detailed structure and the detailed operation of the mammography system 100 in the first embodiment can be suitably changed without departing the gist of the present invention.

[Second Embodiment]

In the second embodiment, described is an example in which radiography performance information is related to radiographing order information with information of a radiographic part/direction as key information, and a mamma image, radiographing order information and radiography performance information are related to one another without using a cassette ID.

Since a system structure of a mammography system in the second embodiment is the same as the mammography system 100 described in the first embodiment, an identical symbol is added to each component, description of the component having the identical symbol is omitted and only a different functional part will be described.

The control unit 31 of the controller 30 loads a second radiography processing program (see FIG. 13) from the storage unit 36, develops it into the RAM 35, and integrally controls a process operation in cooperation with the program. In the second radiography process, radiography performance information is related to radiographing order information based on information of a radiographic part/direction included in the radiography performance information transmitted from the mammography apparatus 10, and information of a radiographic part/direction included in the radiographing order information, and then the related radiographing order information and the related radiography performance information are stored in the order file 361. Then, the radiographing order information and the radiography performance information are related to a mamma image so as to make a turn of relating radiography performance information, which is a radiographing turn, correspond to a turn of receiving the mamma images from the reading apparatus 50, which is a reading turn.

The storage unit 36 stores, in addition to a system program, the second radiography processing program, data processed by each program and the like.

Next, an operation in the second embodiment will be described.

With reference to FIG. 13, the second radiography process performed by the mammography system 100 will be described. Here, as well as the first embodiment, if there are a plurality of pieces of radiographing order information corresponding to one patient, it is assumed that all the radiographic parts/directions in each radiographing order information are different from one another.

In the second radiography process shown in FIG. 13, the controller 30 displays patients to be radiographed in a list form on the display unit 33, based on radiographing order information stored in the order file 361. If a radiographic technician selects and inputs a patient of a radiography subject at the input unit 32 among the list-displayed patients, the controller 30 displays radiographing order information corresponding to the selected patient in a list form (Step T1). Here, it is assumed that displayed in a list form are four different pieces of radiographing order information, whose radiographic parts/directions are a left mamma in an up-down direction, a left mamma in an in-out direction, a right mamma in an up-down direction, and a right mamma in an in-out direction, as related to the selected patient.

Next, the radiographic technician travels to the mammography apparatus 10, sets a cassette c to the radiographic platform 6 and operates the input unit 3b for inputting a radiography instruction. At the time of radiography, the part/direction specifier 70 described in the first embodiment may be used. Since its using method, effect and the like are the same as the first embodiment, the description of the part/direction specifier 70 is omitted. The mammography apparatus 10 performs one time of radiography, which is radiography at one radiographic part/direction (Step T2), and its radiography performance information is transmitted to the controller 30 (Step T3).

Figure 14:
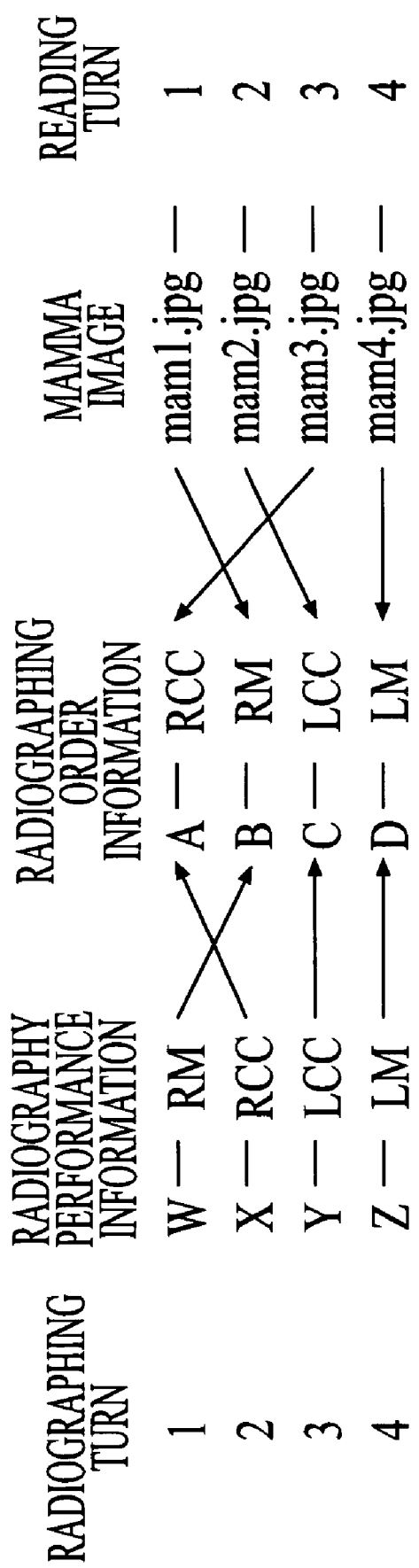
FIG. 14 is a view describing correspondence among a mamma image, radiographing order information and radiography performance information in the second radiography process.
Figure 16:
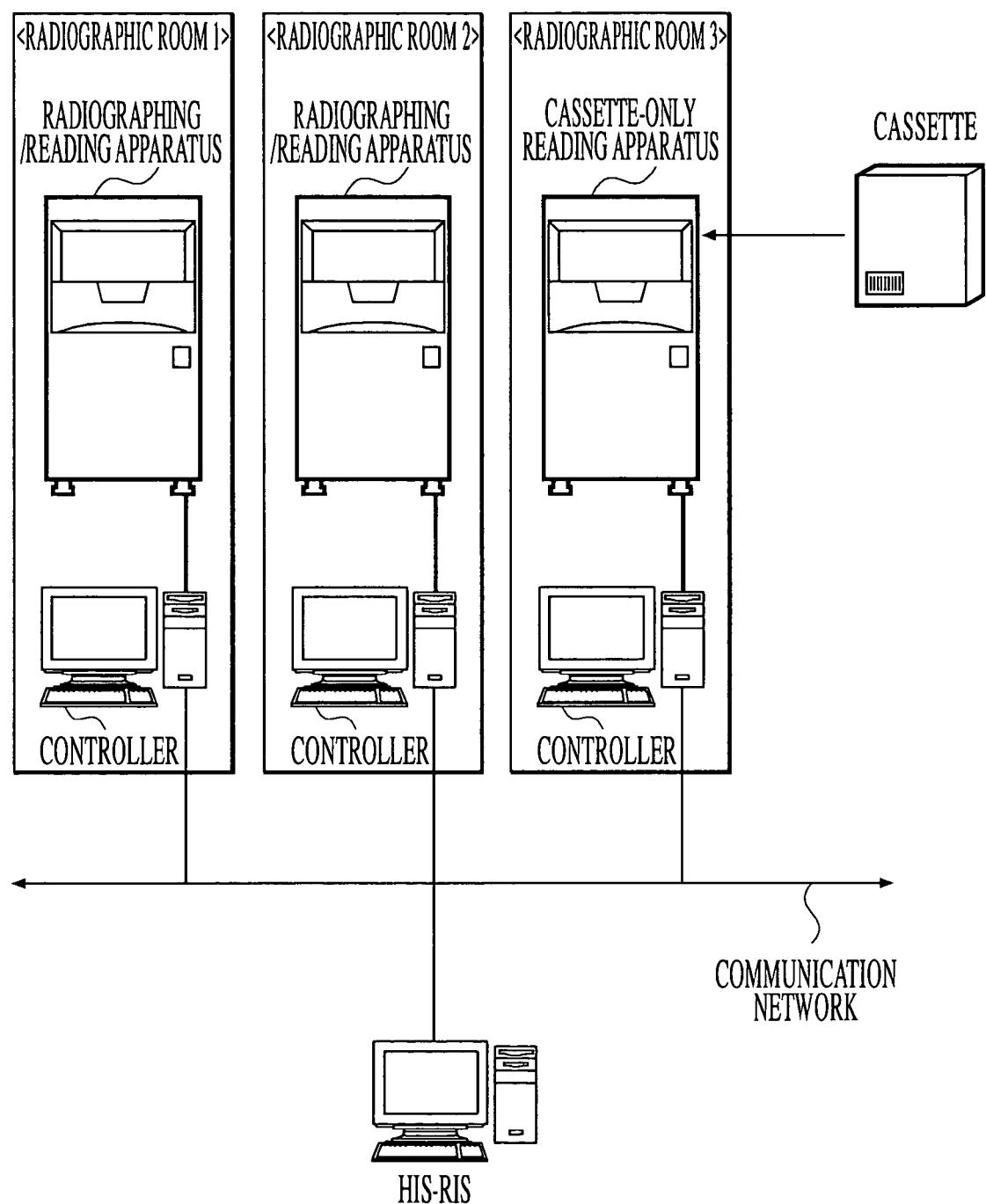
FIG. 16 is a system structure of a conventional radiography system.

The controller 30 relates radiographing order information and radiography performance information based on information of a radiographic part/direction included in the radiography performance information (Step T4). For example, as shown in FIG. 14, corresponding to one selected patient, provided are pieces of radiographing order information having different radiographic parts/directions from one another, which are A (radiographic part/direction; RCC), B (radiographic part/direction; RM), C (radiographic part/direction; LCC) and D (radiographic part/direction; LM). When the mammography apparatus 10 performs radiography in the turn of RM, RCC, LCC and LM, based on the radiographic part/direction, the controller 30 sequentially relates radiographing order information B to radiography performance information W, radiographing order information A to radiography performance information X, radiographing order information C to radiography performance information Y, and radiographing order information D to radiography performance information Z.

On the other hand, the radiographic technician travels to the reading apparatus 50 with a cassette c which has completed radiography, sets the cassette c to the reading apparatus 50 and inputs a reading instruction. In other words, the reading is performed at each time of radiography. The reading apparatus 50 reads a mamma image from the cassette c (Step T5), and the read mamma image is transmitted to the controller 30 (Step T6). When receiving the mamma image from the reading apparatus 50, the controller 30 relates the received mamma image to radiographing order information which was related to radiography performance information just before receiving the mamma image (Step T7). In other words, a mamma image, radiographing order information and radiography performance information are related to one another so as to make a radiographing turn correspond to a reading turn.

For example, in accordance with the description above, as shown in FIG. 14, the radiographing order information B which is related to the radiography performance information W corresponding to the first turn of radiography, is related to a data file mam1.jpg of a mamma image which has been read at first.

When the reading apparatus 50 completes reading a mamma image, the radiographic technician travels back to the mammography apparatus 10 with a not-radiographed cassette c. Then radiography is performed at a next radiographic part/direction with the cassette c. The mammography apparatus 10 determines whether the next radiography has been instructed (Step T8), and if the next radiography has been instructed (T8; Y), the process advances to Step T2 to perform one time of radiography. In this way, processes of Steps T2 to T8 are repeated until radiography to one patient at all the radiographic parts/directions is completed.

Then, when radiography at all the radiographic parts/directions is completed, the radiographic technician returns to the controller 30 in order to confirm correspondence among a mamma image, radiographing order information and radiography performance information. When all the radiographing order information corresponding to one patient is related to a mamma image and radiographing order information, the controller 30 displays the confirmation screen 331 shown in FIG. 9 on the display unit 33 for confirming correspondence among the related mamma image, radiographing order information and radiography performance information (Step T9). Since the confirmation screen 331 has the same screen structure as described in the first embodiment, the detailed description thereof is omitted.

The radiographic technician looks at a radiographed mamma image to confirm correspondence among the mamma image, radiographing order information and radiography performance information according to its radiographic part/direction. If the correspondence is adequate, the radiographic technician pushes the OK button d6 displayed at the lower part of the screen.

When the OK button d6 is pushed on the confirmation screen 331, the controller 30 displays a patient selecting screen for selecting a patient of a next radiography subject on the display unit 33. If it is necessary to advance to radiography on a next patient, the radiographic technician selects a patient of a radiography subject on the patient selecting screen. If it is necessary to end radiography, the radiographic technician inputs an instruction to end the radiography.

The controller 30 determines whether a patient to be radiographed next has been selected (Step T10). If the patient has been selected (Step T10; Y), the process returns to Step T2 to perform radiography process on the selected patient repeatedly. If the patient has not been selected (step T10; N), the present process is finished. After the process is finished, a mamma image is stored in a predetermined database for storing images. In the meantime, together with the mamma image, radiographing order information related to the mamma image, radiography performance information related to the same are stored as accompanying information of the mamma image in the predetermined database.

As mentioned, if a plurality of pieces of radiographing order information having different radiographic parts/directions from one another are provided corresponding to one selected patient, immediately after radiography at one part/direction is performed with the use of a cassette c, the reading apparatus 50 reads a mamma image from the cassette c. Thereby, the controller 30 relates the radiographing order information and the radiography performance information to each other with information of the radiographic part/direction as key information, and relates the mamma image, the radiographing order information and the radiography performance information to one another so as to make the radiographing turn correspond to the reading turn. As a result, it is possible to relate a mamma image, radiographing order information and radiography performance information to one another without using a cassette ID. Therefore, it is possible to omit an operation of cassette registration.

Further, in the conventional radiography, after selecting radiographing order information which radiography is to be performed based on at the controller 30, the radiographic technician travels to the mammography apparatus 10 for performing radiography, and then the radiographic technician travels to the reading apparatus 50 for reading a mamma image, and further the radiographic technician travels back to the controller 30 for selecting radiographing order information. Therefore, an operation is complicated due to frequent travels. However, in the second embodiment, once radiography is performed by the mammography apparatus 10, the controller 30 automatically relates radiographing order information and radiography performance information to each other, and when the reading apparatus 50 reads a mamma image, the controller 30 automatically relates the mamma image read by the reading apparatus 50, the radiographing order information and the radiography performance information to one another. Therefore, since a radiographic technician does not need to return to the controller 30 until all the radiography corresponding to one patient is completed while only traveling back and forth between the mammography apparatus 10 and the reading apparatus 50, it is possible to improve efficiency of a radiography operation.

Further, since reading a mamma image is performed after each time of radiography, it is not necessary for a radiographic technician to memorize which radiographic part/direction a mamma image at is recorded in a cassette c, or record it on paper. Therefore, it is possible to reduce a burden on an operation by the radiographic technician.

Here, the described contents in the first and second embodiments are a suitable example of the mammography system to which the present invention is applied, and the present invention is not limited to the example.

For example, in the mammography apparatus 10, by issuing a radiography number which indicates a radiographing turn to each radiography, transmitting radiography performance information including the radiography number as key information to the controller 30, and in the controller 30, by storing a radiographing turn of radiography to be performed based on radiographing order information, the radiographing turn being inputted at the input unit 3b by a radiographic technician with the radiographing order information related to as key information in the order file 361, the radiographing order information and the radiography performance information may related to each other with the radiographing turn as key information. In other words, by the input unit 3b, it is possible to achieve a radiographing turn input section.

Further, in the description above, in the mammography apparatus 10, a radiographic part/direction is determined based on a rotation angle of the radiographing unit 1. However, a way of determining a radiographic part/direction is not limited to the description above. For example, by transmitting information of a rotation angle detected in the mammography apparatus 10, a radiographic part/direction may be determined based on the information of the rotation angle in the controller 30.

Further, in order to relate radiographing order information and a mamma image to each other, by performing radiography in the mammography apparatus 10 with the use of a lead plate to specify a radiographic part/direction, and image-analyzing a mamma image with the lead plate in the controller 30, a radiographic part/direction may be determined.

For example, as shown in FIG. 15A, lead plates p1 and p2 are attached to a position which is an upper part of a cassette c to be used for radiography, the position facing a subject. The lead plate p1 is used to specify a radiographic part. The lead plate p2 is used to specify a radiographic direction. The lead plate p1 is formed in approximately rectangular, and the lead plate p2 is formed in approximately square with length of a side approximately one-third as long as that of a longer side of the lead plate p1.

First, an example of attaching the lead plate p1 in the case of specifying a radiographic part will be described. When a left mamma is to be radiographed, the lead plate p1 is attached at the left side seen from a subject. When a right mamma is to be radiographed, the lead plate p1 is attached at the right side seen from the subject.

Next, an example of attaching the lead plate p2 in the case of specifying a radiographic direction will be described. When radiography in an up-down direction (CC) is to be performed, the lead plate p2 is attached below-left of the lead plate p1. When radiography in an oblique direction (MLO) is to be performed, the lead plate p2 is attached below-center of the lead plate p1. When radiography in an in-out direction (M) is to be performed the lead plate p2 is attached below-right of the lead plate p1.

FIGS. 15B to 15D show mamma images obtained as a result of performing radiography with the lead plates p1 and p2 attached to a cassette c according to radiographic parts/directions. FIGS. 15B to 15D are radiographed images of a left mamma, and FIG. 15B is an image radiographed in an up-down direction, FIG. 15C is an image radiographed in an oblique direction, and FIG. 15D is an image radiographed in an in-out direction. As shown in FIGS. 15B to 15D, on the radiographed images, areas where the lead plates p1 and p2 are radiographed have low density due to little radiation transmittance. Thereby, it is distinguishable from a plain area having high density. As a result, an image pattern with the lead plates p1 and p2 radiographed is characteristic of a radiographic part/direction.

In this way, the controller 30 recognizes a pattern in a mamma image with a radiographic part/direction specified by the lead plates p1 and p2 to determine a radiographic part/direction. When a radiographic part/direction is determined, radiographing order information and a mamma image can be related to each other with the radiographic part/direction as key information. Here, the reading apparatus 50 may comprise a pattern recognition function of an image for determining a radiographic part/direction at the side of the reading apparatus 50. However, if the mammography system has a system structure in which a plurality of controllers 30 and a plurality of reading apparatuses 50 are connected to each other through a communication network, preferably a reading apparatus which primarily reads more mamma images comprises the pattern recognition function.

Further, on a mamma image in which the part/direction specifier 70 described in the first embodiment is radiographed, a radiographic part/direction may be determined by recognizing a pattern of a radiographing position of the metal sphere 72 radiographed in an up-down direction, an oblique direction or an in-out direction. However, since the above-mentioned lead plates p1 and p2 are in general widely used as a marker in radiography, it has high versatility.

Further, in the above-described mammography system 100, shown is the example of the mammography apparatus 10 performing radiography with the use of a cassette c. However, the mammography apparatus 10 may comprise another type of a radiation detector without using the cassette c, and both radiography and reading a mamma image may be performed in the mammography apparatus 10.

As another type of a radiation detector, a flat panel detector (hereinafter, it is referred to as FPD), a phosphor plate and the like can be cited. The FPD has a structure in which radiation detecting devices for generating electric charge according to irradiated radiation intensity and condensers for accumulating the electric charge generated by the radiation detecting devices are arranged two-demensionally. With the FPD placed on the radiographic platform 6, an image signal obtained from the FPD is outputted to the main unit 3 and image data is generated in the main unit 3. Further, if the phosphor plate is used, a reading unit is provided for obtaining an image signal by irradiating laser beam to the phosphor plate, detecting the accumulated radiation energy as fluorescence, and photoelectrically converts the fluorescence.

If the mammography system has a structure in which the mammography apparatus 10 performs both radiography and reading, a radiographed and then read mamma image is related to radiography performance information and transmitted to the controller 30. The controller 30 relates radiographing order information and the radiography performance information based on information of a radiographic part/direction included in the radiography performance information. In other words, since a mamma image, radiographing order information and radiography performance information are related to one another with a radiographic part/direction as key information after each time of radiography, it is possible for a radiographic technician to omit an operation of selecting radiographing order information to be related to radiography performance information at each time of radiography in the controller 30. Thereby, it is possible to improve efficiency of a radiography operation.

And so forth, the detailed structure and the detailed operation of the mammography system 100 in the first and second embodiments may be suitably changed without departing the gist of the present invention.

The entire disclosure of Japanese Patent Application No. Tokugan 2003-120246 filed on Apr. 24, 2003 including a specification, claims, drawings and summaries are incorporated herein by reference in their entirety.

What is claimed is:

1. A mammography system comprising:
   a mammography apparatus for radiographing a mamma image of a patient by irradiating radiations and for recording the mamma image in a cassette;
   a reading apparatus for reading the mamma image from the cassette; and
   a controller for obtaining the read mamma image by controlling the reading apparatus, the controller being connected to the mammography apparatus and the reading apparatus,
   wherein the mammography apparatus comprises a communication section for transmitting radiography performance information to the controller, the radiography performance information including first key information for relating the radiography performance information and radiographing order information to each other, and
   the controller comprises:
   a storage section for storing the radiographing order information including second key information for relating the radiography performance information and the radiographing order information to each other; and
   a controlling section for relating the radiography performance information and the radiographing order information based on the first key information included in the radiography performance information transmitted from the mammography apparatus and the second key information included in the stored radiographing order information.

2. The system of claim 1, wherein
   the reading apparatus comprises a communication section for reading the mamma image and identification information of the cassette from the cassette, for relating the identification information of the cassette to the mamma image, and for transmitting the related mamma image and the related identification information of the cassette, to the controller;
   the controller comprises an identification information input section for inputting the identification information of the cassette to be used in radiography; and
   the controlling section relates the inputted identification information of the cassette to the radiographing order information, and relates the mamma image, the radiographing order information and the radiography performance information to one another based on the identification information of the cassette related to the radiographing order information and the identification information of the cassette related to the mamma image transmitted from the reading apparatus.

3. The system of claim 2, wherein the controller comprises a display section for displaying correspondence among the mamma image, the radiographing order information and the radiography performance information that are related to one another by the controlling section.

4. The system of claim 1, wherein the communication section in the mammography apparatus transmits the radiography performance information including the first key information to the controller at each time of radiography,
   the reading apparatus comprises a communication section for transmitting the mamma image to the controller at each time of reading the mamma image, and
   the controlling section in the controller relates the radiographing order information and the radiography performance information to each other based on the first key information and the second key information, and relates the mamma image, the radiographing order information and the radiography performance information to one another so as to make a radiographing turn of the mamma image correspond to a reading turn of the mamma image.

5. The system of claim 1, wherein the first key information and the second key information include information of at least one of a radiographic part and a radiographic direction.

6. The system of claim 5, wherein
   the mammography apparatus comprises:
   an angle detecting section for detecting an angle of a radiographic platform to place a subject on; and
   a determination section for determining at least one of the radiographic part and the radiographic direction based on the detected angle, and
   the communication section in the mammography apparatus transmits the information of at least one of the radiographic part and the radiographic direction as the first key information to the controller.

7. The system of claim 5, wherein
   the mammography apparatus comprises an angle detecting section for detecting an angle of a radiographic platform to place a subject on, and
   the controller comprises a determination section for determining at least one of the radiographic part and the radiographic direction based on information of the detected angle.

8. The system of claim 5, wherein
   the mammography apparatus comprises a part/direction input section for inputting the information of at least one of the radiographic part and the radiographic direction, and
   the communication section in the mammography apparatus transmits the inputted information of at least one of the radiographic part and the radiographic direction as the first key information to the controller.

9. The system of claim 5, wherein
the first key information and the second key information include left-right information for indicating whether the radiographic part is a right mamma or a left mamma,
the communication section in the mammography apparatus transmits the radiography performance information including the left-right information to the controller,
the storage section in the controller stores the radiographing order information including the left-right information for indicating whether the radiographic part is the right mamma or the left mamma, and
the controlling section in the controller relates the radiography performance information and the radiographing order information based on the left-right information included in the radiography performance information transmitted from the mammography apparatus and the left-right information included in the stored radiographing order information.

10. The system of claim 9, wherein the mammography apparatus comprises a left-right information input section for inputting the left-right information.

11. The system of claim 1, wherein the communication section in the mammography apparatus transmits information indicating a radiographing turn of the mamma image as the first key information to the controller,
the controller comprises a radiographing turn input section for inputting the radiographing turn of radiography to be performed based on the radiographing order information,
the storage section in the controller stores the radiographing order information and the inputted radiographing turn so as to relate the radiographing order information and the inputted radiographing turn to each other, and
the controlling section in the controller relates the radiographing order information and the radiography performance information to each other so as to make the radiographing turn included in the radiography performance information transmitted from the mammography apparatus correspond to the radiographing turn related to the stored radiographing order information.

12. The system of claim 11, wherein
the communication section in the reading apparatus transmits the mamma image read from the cassette in a reading turn of the mamma image from the cassette, and
the controlling section in the controller relates the mamma image, the radiographing order information and the radiography performance information to one another so as to make the radiographing turn of the mamma image correspond to the reading turn of the mamma image.

13. The system of claim 1, wherein radiography is performed with a part/direction specifier attached to the cassette, the part/direction specifier indicating a radiographic part and a radiographic direction in the mamma image.

14. The system of claim 1, wherein radiography is performed with a part/direction specifier attached to one of the radiographic platform of the mammography apparatus and a pressure plate for compressing a mamma, the part/direction specifier indicating a radiographic part and a radiographic direction in the mamma image.

15. A mammography system comprising:
a mammography apparatus for radiographing a mamma image of a patient by irradiating radiations and for reading the mamma image as digital data; and
a controller for obtaining the mamma image, the controller connected to the mammography apparatus,
wherein the mammography apparatus comprises a communication section for relating radiography performance information to the read mamma image, the radiography performance information including first key information for relating the radiography performance information and radiographing order information, and for transmitting the related radiography performance information and the related mamma image, to the controller, and
the controller comprises:
a storage section for storing the radiographing order information including second key information for relating the radiography performance information and the radiographing order information; and
a controlling section for relating the mamma image, the radiographing order information and the radiography performance information to one another based on the first key information included in the radiography performance information transmitted from the mammography apparatus and the second key information included in the stored radiographing order information.

16. The system of claim 15, wherein
the first key information and the second key information include left-right information for indicating whether a radiographic part is a right mamma or a left mamma,
the communication section in the mammography apparatus transmits the radiography performance information including the left-right information to the controller,
the storage section in the controller stores the radiographing order information including the left-right information, and
the controlling section in the controller relates the mamma image, the radiographing order information and the radiography performance information to one another based on the left-right information included in the radiography performance information transmitted from the mammography apparatus and the second key information included in the stored radiographing order information.

17. A method for managing information in a mammography system comprising a mammography apparatus for radiographing a mamma image by irradiating radiations and for recording the mamma image in a cassette, a reading apparatus for reading the mamma image from the cassette, and a controller for obtaining the read mamma image by controlling the reading apparatus, the controller being connected to the mammography apparatus and the reading apparatus, the method comprising:
transmitting radiography performance information including first key information from the mammography apparatus to the controller, the first key information for relating the radiography performance information and radiographing order information to each other;
storing the radiographing order information including second key information in a storage section of the controller, the second key information for relating the radiography performance information and the radiographing order information; and
relating the radiography performance information and the radiographing order information to each other based on the first key information included in the radiography performance information transmitted from the mammography apparatus and the second key information included in the stored radiographing order information, in the controller.

18. The method of claim 17, further comprising:
reading the mamma image and identification information of the cassette from the cassette, in the reading apparatus;
transmitting the mamma image and the identification information of the cassette to the controller so as to relate the mamma image and the identification information of the cassette to each other;
inputting the identification information of the cassette to be used in radiography, in the controller;
relating the inputted identification information of the cassette to the radiographing order information, in the controller; and
relating the mamma image, the radiographing order information and the radiography performance information to one another based on the identification information of the cassette related to the radiographing order information and the identification information of the cassette related to the mamma image transmitted from the reading apparatus, in the controller.

19. The method of claim 18, further comprising displaying correspondence among the mamma image, the radiographing order information and the radiography performance information that are related to one another, on a display section of the controller.

20. The method of claim 17, further comprising:
transmitting the radiography performance information including the first key information to the controller at each time of radiography;
transmitting the mamma image to the controller at each time that the reading apparatus reads the mamma image; and
relating the mamma image, the radiographing order information and the radiography performance information to one another so as to make a radiographing turn of the mamma image correspond to a reading turn of the mamma image after the radiographing order information and the radiography performance information are related to each other based on the first key information and the second key information.

21. The method of claim 17, wherein the first key information and the second key information include information of at least one of a radiographic part and a radiographic direction.

22. The method of claim 21, further comprising:
detecting an angle of a radiographic platform to place a subject on, in the mammography apparatus; and
determining at least one of the radiographic part and the radiographic direction according to the detected angle, in the mammography apparatus,
wherein the transmitting the radiography performance information including the first key information includes transmitting information of the determined at least one of the radiographic part and the radiographic direction as the first key information to the controller.

23. The method of claim 21, further comprising:
detecting an angle of a radiographic platform to place a subject on, in the mammography apparatus; and
determining at least one of the radiographic part and the radiographic direction based on information of the detected angle, in the mammography apparatus.

24. The method of claim 21, further comprising:
inputting information of at least one of the radiographic part and the radiographic direction, in the mammography apparatus,
wherein the transmitting the radiography performance information including the first key information includes transmitting the inputted information of at least one of the radiographic part and the radiographic direction as the first key information to the controller.

25. The method of claim 17, further comprising inputting a radiographing turn of radiography to be performed based on the radiographing order information, in the controller,
wherein the transmitting the radiography performance information including the first key information includes transmitting information which indicates a radiographing turn of the mamma image as the first key information to the controller,
the storing the radiographing order information includes storing the radiographing order information and the inputted radiographing turn so as to relate the radiographing order information and the radiographing turn to each other, in the storage section of the controller, and
the relating the radiography performance information and the radiographing order information to each other includes relating the radiography performance information and the radiographing order information to each other so as to make the radiographing turn included in the radiography performance information correspond to the radiographing turn related to the stored radiographing order information.

26. The method of claim 25, further comprising:
transmitting the mamma image read from the cassette from the reading apparatus to the controller, in a reading turn of the mamma image from the cassette; and
relating the mamma image, the radiographing order information and the radiography performance information to one another so as to make the radiographing turn of the mamma image correspond to the reading turn of the mamma image, in the controller.

27. The method of claim 17, further comprising performing radiography with a part/direction specifier attached to the cassette, the part/direction specifier indicating a radiographic part and a radiographic direction in the mamma image.

28. The method of claim 17, further comprising performing radiography with a part/direction specifier attached to one of the radiographic platform of the mammography apparatus and a pressure plate for compressing a mamma, the part/direction specifier indicating a radiographic part and a radiographic direction in the mamma image.

29. A method for managing information in a mammography system comprising a mammography apparatus for radiographing a mamma image of a patient by irradiating radiations and for reading the mamma image as digital data, and a controller for obtaining the read mamma image from the mammography apparatus, the controller being connected to the mammography apparatus, the method comprising:
transmitting radiography performance information including first key information and the read mamma image so as to relate the radiography performance information and the mamma image to each other, from the mammography apparatus to the controller, the first key information for relating the radiography performance information and radiographing order information to each other;
storing the radiographing order information including second key information in a storage section of the controller, the second key information for relating the radiography performance information and the radiographing order information; and relating the mamma image, the radiographing order information, the radiography performance information to one another based on the first key information included in the radiography performance information transmitted from the mammography apparatus and the second key information included in the radiographing order information, in the controller.

30. A method for managing information in a mammography system comprising a mammography apparatus for radiographing a mamma image of a patient by irradiating radiations and for recording the mamma image in a cassette, a reading apparatus for reading the mamma image from the cassette, and a controller for storing radiographing order information including second key information for relating radiography performance information and the radiographing order information and for obtaining the read mamma image by controlling the reading apparatus, when a plurality of mamma images corresponding to one patient are radiographed by using a plurality of cassettes, at each time of radiographing one of the plurality of mamma images in the mammography apparatus, the method comprising:

transmitting the radiography performance information including first key information, from the mammography apparatus to the controller, the first key information for relating the radiography performance information and radiographing order information to each other; and relating the obtained mamma image, the radiographing order information and the radiography performance information to one another based on the first key information included in the radiography performance information transmitted from the mammography apparatus and the second key information included in the radiographing order information, in the controller.

* * * * *